US012716057B2

(12) United States Patent
Zhang et al.

(10) Patent No.: US 12,716,057 B2
(45) Date of Patent: Aug. 25, 2026

(54) METHOD FOR CULTURING GYNAECOLOGICAL TUMOUR PRIMARY CELLS AND MATCHING CULTURE MEDIUM

(71) Applicant: GeneX Health Co., Ltd, Beijing (CN)

(72) Inventors: Hanshuo Zhang, Beijing (CN); Shenyi Yin, Beijing (CN)

(73) Assignee: GENEX HEALTH CO., LTD, Beijing (CN)

( * ) Notice: Subject to any disclaimer, the term of this patent is extended or adjusted under 35 U.S.C. 154(b) by 1148 days.

(21) Appl. No.: 17/772,203

(22) PCT Filed: Nov. 4, 2020

(86) PCT No.: PCT/CN2020/126391

§ 371 (c)(1),
(2) Date: Jun. 28, 2022

(87) PCT Pub. No.: WO2021/088847

PCT Pub. Date: May 14, 2021

(65) Prior Publication Data

US 2022/0403342 A1 Dec. 22, 2022

(30) Foreign Application Priority Data

Nov. 5, 2019 (CN) ......................... 201911069251.4
Nov. 5, 2019 (CN) ......................... 201911069291.9

(51) Int. Cl.
*C12N 5/09* (2010.01)

(52) U.S. Cl.
CPC ........ *C12N 5/0693* (2013.01); *C12N 2500/32* (2013.01); *C12N 2500/60* (2013.01); *C12N 2501/11* (2013.01); *C12N 2501/115* (2013.01); *C12N 2501/12* (2013.01); *C12N 2501/39* (2013.01); *C12N 2501/392* (2013.01)

(58) Field of Classification Search
CPC .................................................... C12N 5/0693
See application file for complete search history.

(56) References Cited

U.S. PATENT DOCUMENTS 11,753,626 B2 * 9/2023 Chen .................. G01N 33/5011 435/375
2011/0033932 A1 2/2011 Kira et al.
2017/0226472 A1 8/2017 Marchal Corrales et al.

FOREIGN PATENT DOCUMENTS

CN 103966167 A 8/2014
CN 104640974 A 5/2015
CN 106414707 A 2/2017
CN 107208026 A 9/2017
CN 108884445 A 11/2018

OTHER PUBLICATIONS

Shi Minfeng; Isolation, identification and sensitivity to chemotherapeutic drugs of human ovarian cancer tumor stem-like cells [D]; Zhejiang University School of Medicine, Zhejiang University, Sep. 15, 2010, 3 pgs.
International Search Report issued in corresponding International Application No. PCT/CN2020/126391; mailed Feb. 4, 2021; 8 pgs.

* cited by examiner

*Primary Examiner* — Christopher M Babic
*Assistant Examiner* — Hanan Isam Abuzeineh
(74) *Attorney, Agent, or Firm* — HAUPTMAN HAM, LLP

(57) ABSTRACT

A method for culturing primary gynecological tumor cells and culture medium used therein. The method includes using mild cell dissociation reagents to treat a gynecological solid tumor tissue, to ensure the vitality of tumor cells in the tissue to the greatest extent; preparing a special serum-free medium, and using a suspension culture system to culture solid tumor cells derived from a gynecological tumor in vitro to ensure the normal expansion of tumor cells and eliminate interference from normal cells to the greatest extent. The primary gynecological tumor cell culture obtained by the method of the present invention can be used for various cell-based in vitro experiments, second-generation sequencing, construction of animal models, construction of cell lines and the like. It is foreseeable that this culture method has broad application prospects in the fields of gynecological tumor research and clinical diagnosis and treatment.

16 Claims, 5 Drawing Sheets

METHOD FOR CULTURING GYNAECOLOGICAL TUMOUR PRIMARY CELLS AND MATCHING CULTURE MEDIUM

RELATED APPLICATIONS

The present application is a U.S. National Phase of International Application Number PCT/CN2020/126391 filed Nov. 4, 2020, and claims priority to Chinese Application Numbers 201911069251.4 and 201911069291.9, both filed on Nov. 5, 2019.

TECHNICAL FIELD

The present invention relates to the field of biotechnology, in particular to a method for culturing primary gynecological tumor cells and a culture medium used therein.

BACKGROUND OF THE INVENTION

Common gynecological tumors include breast cancer, ovarian cancer endometrial cancer, etc. According to statistics from the National Cancer Center in 2018, in 2014, breast cancer accounted for 16.5% of the incidence of female malignant tumors in China, and the mortality rate reached 7.8%, ranking first and fifth respectively in female tumors. At present, the 5-year survival rate of breast cancer in China is only 73.1% (vs. 90% in US), which is still far behind developed countries. In addition, the incidence of ovarian cancer in China accounts for 2.5% of female malignant tumors, and has increased by 30% in the past decade. These gynecological tumors pose serious challenges to the life and health of women in China.

Although scientific research and medical institutions all over the world have made great efforts to study the etiology and occurrence and development of gynecological tumors, people still know little about these diseases. Gynecological tumors are a kind of complex diseases. The occurrence and development of gynecological tumors are a dynamic process, involving the interaction of many signal molecules, forming a complex molecular regulation network, and are also affected by external environmental factors. The etiology and occurrence and development of gynecological tumors have strong individual differences and cannot be generalized. Therefore, it is a trend in the field of gynecological tumor research and even in the field of gynecological tumor diagnosis and treatment to use the primary cell culture of gynecological solid tumor as a model for individualized and precise research.

The existing primary tumor cell culture technologies mainly include 2D culture, 3D culture, and reprogramming culture. These methods all face the problems of extremely long culture cycle, low culture success rate, and difficulty in removing miscellaneous cells to varying degrees.

SUMMARY OF THE INVENTION

In order to effectively solve the above technical problems, the present invention provides a new technology for culturing primary gynecological solid tumor cells and reagents used therein. The core of the technology is: (1) using mild cell dissociation reagents to treat a gynecological solid tumor tissue, to ensure the vitality of tumor cells in the tissue to the greatest extent; (2) preparing a special serum-free medium, and using a suspension culture system to culture primary gynecological tumor cells in vitro, to ensure the normal expansion of tumor cells and eliminate interference from normal cells to the greatest extent.

In a first aspect, the present invention provides a culture medium.

The culture medium provided in the present invention is culture medium A or culture medium B.

The culture medium A is composed of a solution containing three antibiotic and antimycotic agents (penicillin-streptomycin-amphotericin B), HEPES, GlutaMax, human recombinant protein EGF, human recombinant protein bFGF, human recombinant protein HGF, human recombinant protein MSP, hydrocortisone, N-2 Supplement, Y-27632, progesterone, β-estradiol and a basic culture medium for human cell culture (such as Advanced DMEM/F12 culture medium); wherein, the final concentration of penicillin in the solution containing three antibiotic and antimycotic agents is 100-200 U/mL (such as 100 U/mL); the final concentration of streptomycin in the solution containing three antibiotic and antimycotic agents is 100-200 μg/mL (such as 100 μg/mL); the final concentration of amphotericin B in the solution containing three antibiotic and antimycotic agents is 250-250 ng/mL (such as 250 ng/mL); the final concentration of HEPES is 8-12 mM (such as 10 mM); the final concentration of GlutaMax is 0.8-1.2% (such as 1%, % represents the volume percentage); the final concentration of the human recombinant protein EGF is 10-100 ng/mL; the final concentration of the human recombinant protein bFGF is 10-50 ng/mL; the final concentration of the human recombinant protein HGF is 5-25 ng/mL; the final concentration of the human recombinant protein MSP is 5-25 ng/mL; the final concentration of hydrocortisone is 1-10 μg/mL; the final concentration of N-2 Supplement is 1% (volume percentage); the final concentration of Y-27632 is 5-20 μM; the final concentration of progesterone is 50-100 nM; the final concentration of β-estradiol is 10-50 nM; and the rest is the basic culture medium for human cell culture (such as Advanced DMEM/F12 culture medium).

The culture medium B is composed of a solution containing three antibiotic and antimycotic agents (penicillin-streptomycin-amphotericin B solution), HEPES, GlutaMax, human recombinant protein EGF, human recombinant protein bFGF, human recombinant protein HGF, human recombinant protein MSP, N-acetyl-L-cysteine, N-2 Supplement, Y-27632, progesterone, β-estradiol and a basic culture medium for human cell culture (such as Advanced DMEM/F12 culture medium); wherein, the final concentration of penicillin in the solution containing three antibiotic and antimycotic agents is 100-200 U/mL (such as 100 U/mL); the final concentration of streptomycin in the solution containing three antibiotic and antimycotic agents is 100-200 μg/mL (such as 100 μg/mL); the final concentration of amphotericin B in the solution containing three antibiotic and antimycotic agents is 250-250 ng/mL (such as 250 ng/mL); the final concentration of HEPES is 8-12 mM (such as 10 mM); the final concentration of GlutaMax is 0.8-1.2% (such as 1%, % represents the volume percentage); the final concentration of the human recombinant protein EGF is 10-100 ng/mL; the final concentration of the human recombinant protein bFGF is 10-50 ng/mL; the final concentration of the human recombinant protein HGF is 5-25 ng/mL; the final concentration of the human recombinant protein MSP is 5-25 ng/mL; the final concentration of N-acetyl-L-cysteine is 0.5-2 mM; the final concentration of N-2 Supplement is 1% (volume percentage); the final concentration of Y-27632 is 5-20 μM; the final concentration of progesterone is 50-100 nM; the final concentration of f-estradiol is 10-50 nM; and the rest is the basic culture medium for human cell culture (such as Advanced DMEM/F12 culture medium).

Further, the composition of the solution containing three antibiotic and antimycotic agents (penicillin-streptomycin-amphotericin B) is as follows: 10,000 units of penicillin (base), 10,000 μg of streptomycin (base) and 25 μg of amphotericin B/ml. The solution containing three antibiotic and antimycotic agents (penicillin-streptomycin-amphotericin B) is “Antibiotic-Antimycotic, 100X” (such as Gibco #15240062, or other products of the same composition). The “Antibiotic-Antimycotic, 100X” contains 10,000 units of penicillin (base), 10,000 μg of streptomycin (base) and 25 μg of amphotericin B/ml, utilizing penicillin G (sodium salt), streptomycin sulfate and amphotericin B in 0.85% saline as Fungizone® antimycotic. GlutaMAX is an advanced cell culture additive that can directly replace L-glutamine in a cell culture medium. GlutaMAX is “GlutaMAX™ Supplement” (such as Gibco #35050061, or other products of the same composition). The solute of “GlutaMAX™ Supplement” is L-alanyl-L-glutamine (a substitute for L-glutamine) with a concentration of 200 nM, and the solvent is 0.85% NaCl solution. N-2 Supplement is “N-2 Supplement (100X)” (such as Gibco #17502001, or other products of the same composition). “N-2 Supplement (100X)” contains 1 mM human transferrin (Holo), 500 mg/L insulin recombinant full chain, 0.63 mg/L progesterone, 10 mM putrescine and 0.52 mg/L selenite. Y-27632 is “Y-27632 dihydrochloride (an ATP-competitive ROCK-I and ROCK-II inhibitor with Ki of 220 nM and 300 nM, respectively)” (such as MCE #129830-38-2, or other products of the same composition).

In a specific embodiment of the present invention, the article number of the solution containing three antibiotic and antimycotic agents (penicillin-streptomycin-amphotericin B) is Gibco #15240062; the article number of HEPES is Gibco #15630080; the article number of GlutaMAX is Gibco #35050061; the article number of the human recombinant protein EGF is Peprotech AF-100-15-100; the article number of the human recombinant protein bFGF is Peprotech AF-100-18B-50; the article number of the recombinant protein HGF is Peprotech AF-100-39-100; the article number of the human recombinant protein MSP is R&D #352-MS-050; the article number of hydrocortisone is Selleck #S1696; the article number of N-acetyl-L-cysteine is Sigma #A9165; the article number of N-2 Supplement is Gibco #17502001; the article number of Y-27632 is MCE #129830-38-2; the article number of progesterone is Sigma #V900699; the article number of β-estradiol is Sigma #E2758; the article number of Advanced DMEM/F12 culture medium is Gibco #12634010.

Further, the culture medium for culturing primary gynecological tumor cells can be provided in two forms:

First, the culture medium A is a solution containing the solution containing three antibiotic and antimycotic agents (penicillin-streptomycin-amphotericin B), HEPES, GlutaMax, the human recombinant protein EGF, the human recombinant protein bFGF, the human recombinant protein HGF, the human recombinant protein MSP, hydrocortisone, N-2 Supplement, Y-27632, progesterone, β-estradiol and the basic culture medium for human cell culture (such as Advanced DMEM/F12 culture medium).

The culture medium B is a solution containing the solution containing three antibiotic and antimycotic agents (penicillin-streptomycin-amphotericin B), HEPES, GlutaMax, the human recombinant protein EGF, the human recombinant protein bFGF, the human recombinant protein HGF, the human recombinant protein MSP, N-acetyl-L-cysteine, N-2 Supplement, Y-27632, progesterone, β-estradiol and the basic culture medium for human cell culture (such as Advanced DMEM/F12 culture medium).

After preparation, the medium needs to be filtered and sterilized with a 0.22 μM syringe filter (Millipore SLGP033RS), and can be stored at 4° C. for two weeks.

Second, the components of the culture medium exist separately and the culture medium is prepared according to the formula when used.

Further, the human recombinant protein EGF, human recombinant protein bFGF, human recombinant protein HGF and human recombinant protein MSP can be respectively stored in the form of a stock solution (mother solution) (for long-term storage at −80° C.), specifically a 1,000-fold stock solution (mother solution). N-acetyl-L-cysteine, hydrocortisone and Y-27632 can be respectively stored in the form of a stock solution (mother solution) (long-term storage at −20° C.), specifically a 1,000-fold stock solution (mother solution). Progesterone and β-estradiol can be respectively stored in the form of a stock solution (mother solution) (for long-term storage at −20° C.), specifically a 100,000-fold stock solution (mother solution).

1,000× Human recombinant protein EGF stock solution is composed of human recombinant protein EGF, BSA and PBS, wherein the final concentration of the human recombinant protein EGF is 20 μg/mL, the final concentration of BSA is 0.01 g/mL, and the rest is PBS.

1,000×Human recombinant protein bFGF stock solution is composed of human recombinant protein bFGF, BSA and PBS, wherein the final concentration of the human recombinant protein bFGF is 20 μg/mL, the final concentration of BSA is 0.01 g/mL, and the rest is PBS.

1,000×Human recombinant protein HGF stock solution is composed of human recombinant protein HGF, BSA and PBS, wherein the final concentration of the human recombinant protein HGF is 20 μg/mL, the final concentration of BSA is 0.01 g/mL, and the rest is PBS.

1,000×Human recombinant protein MSP stock solution is composed of human recombinant protein MSP, BSA and PBS, wherein the final concentration of the human recombinant protein MSP is 20 μg/mL, the final concentration of BSA is 0.01 g/mL, and the rest is PBS.

In the above-mentioned four 1,000-fold stock solutions, BSA can be provided in the form of a 100-fold stock solution (mother solution) (prepared just before use), which is specifically composed of BSA and PBS, wherein the final concentration of BSA (Sigma #A1933) is 0.1 g/mL, and the rest is PBS.

In addition, 1,000×N-acetyl-L-cysteine stock solution is composed of N-acetyl-L-cysteine and ultrapure water, wherein the concentration of N-acetyl-L-cysteine is 0.5 M, and the rest is ultrapure water.

1,000×Y-27632 is composed of Y-27632 and ultrapure water, wherein the final concentration of Y-27632 is 10 mM, and the rest is ultrapure water.

100,000×Progesterone stock solution is composed of progesterone and absolute ethanol, wherein the final concentration of progesterone is 1 mM, and the rest is absolute ethanol.

100,000×β-estradiol stock solution is composed of β-estradiol and absolute ethanol, wherein the final concentration of β-estradiol is 1 mM, and the rest is absolute ethanol.

1,000×hydrocortisone stock solution is composed of hydrocortisone and ultrapure water, wherein the final concentration of hydrocortisone is 0.5 M, and the rest is ultrapure water.

The culture medium is used for culturing primary gynecological tumor cells.

In the culture medium, the term "final concentration" refers to the final concentration in the culture medium.

In a second aspect, the present invention provides a reagent set for culturing primary gynecological tumor cells.

The reagent kit for culturing primary gynecological tumor cells provided in the present invention contains the culture medium described above and at least one of the following reagents: a sample dissociation solution, a sample preservation solution, a cell isolation buffer, a cell digestion solution, a sample washing solution, a digestion stop solution, a cell cryopreservation medium and 1% CY TOP solution.

The sample dissociation solution is composed of collagenase I, collagenase III, collagenase IV and PBS; wherein, the final concentration of collagenase I in the sample dissociation solution is 150-250 U/mL (such as 200 U/mL); the final concentration of collagenase III in the sample dissociation solution is 250-350 U/mL (such as 290 U/mL); the final concentration of collagenase IV in the sample dissociation solution is 150-250 U/mL (such as 200 U/mL); and the rest is PBS.

Among them, the unit U of collagenase (collagenase I, collagenase III or collagenase IV) is defined by the enzymatic activity of the protease: when the collagenase (collagenase I, collagenase III or collagenase IV) is treated with 1 U of the protease for 5 hours at pH 7.5, 37° C., 1 μmol of L-leucine can be released.

In a specific embodiment of the present invention, the article number of collagenase I is Gibco #17100-017; the article number of collagenase III is Solarbio #C8490; the article number of collagenase IV is Gibco #17104-019; the article number of PBS is Gibco #21-040-CVR.

The sample preservation solution is composed of fetal bovine serum, two antibiotics P/S (penicillin-streptomycin), HEPES and HBSS (Hank's balanced salt solution); wherein, the final concentration of fetal bovine serum is 1-5% (such as 2%, % represents volume percentage); the final concentration of penicillin in the two antibiotics P/S is 100-200 U/mL (such as 100 U/mL); the final concentration of streptavidin in the two antibiotics P/S is 100-200 μg/mL (such as 100 μg/mL); the final concentration of HEPES is 8-12 mM (such as 10 mM); and the rest is HBSS.

In a specific embodiment of the present invention, the article number of the two antibiotics P/S is Gibco #15140122; the article number of PBS is Gibco #21-040-CVR.

The cell isolation buffer is composed of two antibiotics P/S (penicillin-streptomycin), heparin sodium and PBS; wherein, the final concentration of penicillin in the two antibiotics P/S (penicillin-streptomycin) is 100-200 U/mL (such as 100 U/mL); the final concentration of streptomycin in the two antibiotics P/S (penicillin-streptomycin) is 100-200 μg/mL (such as 100 μg/mL): the final concentration of heparin sodium is 10 IU/mL; and the rest is PBS.

In a specific embodiment of the present invention, the article number of the two antibiotics P/S (penicillin-streptomycin) is Gibco #15140122; the article number of heparin sodium is Solarbio #H8270; the article number of PBS is Gibco #21-040-CVR.

The composition of the cell digestion solution is as follows: each 10 mL of the cell digestion solution contains 4-6 mL (such as 5 mL) of Accutase, EDTA with a final concentration of 5 mM (such as 10 μL 0.5M EDTA), 1.5-2.5 mL (such as 2 mL) of TrypLE Express, and the rest is PBS.

Further, Accutase is "StemPro™ Accutase™ Cell Dissociation Reagent" (such as Gibco #A11105-01, or other products with the same composition). Accutase is a single-component enzyme, solubilized in D-PBS, 0.5 mM EDTA. TrypLE Express is "TrypLE™ Express Enzyme (1×), no phenol red" (such as Gibco #12604013, or other products with the same composition). "TrypLE™ Express Enzyme (1×), no phenol red" contains 200 mg/L KCl, 200 mg/L $KH_2PO_4$, 8,000 mg/L NaCl, 2160 mg/L $Na_2HPO_4.7H_2O$, 457.6 mg/L EDTA; and also contains a recombinant protease.

In a specific embodiment of the present invention, the article number of Accutase is Gibco #A11105-01; the article number of 0.5M EDTA is Invitrogen #AM9261; the article number of TrypLE Express is Gibco #12604013; the article number of PBS is Gibco #21-040-CVR.

The sample washing solution is composed of two antibiotics P/S (penicillin-streptomycin) and PBS; wherein, the final concentration of penicillin in the two antibiotics P/S is 100-200 U/mL (such as 100 U/mL); the final concentration of streptomycin in the two antibiotics P/S is 100-200 μg/mL (such as 100 μg/mL); and the rest is PBS.

In a specific embodiment of the present invention, the article number of the two antibiotics P/S is Gibco #15140122: the article number of PBS is Gibco #21-040-CVR.

The digestion stop solution is composed of fetal bovine serum, two antibiotics P/S (penicillin-streptomycin) and DMEM medium; wherein, the final concentration of fetal bovine serum is 8-12% (such as 10%, % represents volume percentage); the final concentration of penicillin in the two antibiotics P/S is 100-200 U/mL (such as 100 U/mL); the final concentration of streptomycin in the two antibiotics P/S is 100-200 μg/mL (such as 100 μg/mL); and the rest is DMEM medium.

In a specific embodiment of the present invention, the article number of the two antibiotics P/S is Gibco #15140122; the article number of PBS is Gibco #21-040-CVR.

The cell cryopreservation medium is composed of Advanced DMEM/F12 medium, DMSO and 1% methylcellulose solution; wherein, the volume ratio of Advanced DMEM/F12 medium to DMSO to 1% methylcellulose solution is 20:2:(0.8-1.2), such as 20:2:1; 1% methylcellulose solution is an aqueous methylcellulose solution with a concentration of 1 g/100 ml.

In a specific embodiment of the present invention, the article number of Advanced DMEM/F12 medium is Gibco #12634010; the article number of DMSO is Sigma #D2438; the article number of methylcellulose is Sigma #M7027.

The composition of 1% CYTOP solution is as follows: each 100 mL of 1% CYTOP solution contains 1 mL of CYTOP, and the rest is fluorine oil.

Among them, CYTOP is perfluoro (1-butenylvinylether) polymer. Fluorine oil can be fluorine oil with the article number of 3M #FC40, or other products with the same composition.

In a specific embodiment of the present invention, the article number of CYTOP is specifically Asashi glass #CTL-809M; the article number of fluorine oil is specifically 3M #FC40.

The sample preservation solution can be used for temporary preservation of ex vivo samples, and can maintain the activity of cells in the ex vivo samples for a short period of time. The sample preservation solution can be stored at 4° C. for 1 month after preparation.

The sample washing solution can be used for sample washing and disinfection. The sample washing solution needs to be prepared just before use.

The sample dissociation solution can be used for sample dissociation, and can dissociate the primary gynecological tumor cells in the sample from the tissue. The sample dissociation solution needs to be prepared just before use. Collagenase I, collagenase III and collagenase IV contained can be respectively stored in the form of a stock solution (mother solution) for a long time at −20° C., specifically, the stock solution can be a 10-fold stock solution (mother solution). 10×Collagenase I stock solution is composed of collagenase I and PBS, wherein the final concentration of collagenase I is 2,000 U/mL; 10×collagenase III stock solution is composed of collagenase III and PBS, wherein the final concentration of collagenase III is 2,000 U/mL; 10×collagenase IV stock solution is composed of collagenase IV and PBS, wherein the final concentration of collagenase IV is 2,000 U/mL; in each of them, the rest is PBS. The enzymatic activities of collagenase I, collagenase III and collagenase IV are defined as above.

The cell isolation buffer is used to suspend cells in gynecological tumor pleural effusions and ascites samples. The cell isolation buffer can be stored at 4° C. for 1 month after preparation.

The cell digestion solution can be used for digestion and passage of cell clumps, and can digest gynecological tumor clumps into single cells. The cell digestion solution needs to be prepared just before use.

The digestion stop solution can be used to terminate sample dissociation or cell digestion process. The digestion stop solution can be stored at 4° C. for 1 month after preparation.

The primary gynecological tumor cell culture medium can be used for the culture of primary gynecological tumor cells. The primary gynecological tumor cell culture medium needs to be filtered and sterilized with a 0.22 μM syringe filter (Millipore SLGP033RS) after preparation, and can be stored at 4° C. for two weeks.

The cell cryopreservation medium needs to be prepared just before use, wherein, 1% methylcellulose solution can be stored at 4° C. for a long time.

In the present invention, the term "final concentration" refers to the final concentration of the corresponding component in the corresponding solution.

In a third aspect, the present invention provides use of the culture medium or the reagent set in culturing primary gynecological tumor cells.

In a fourth aspect, the present invention provides a method for culturing primary gynecological tumor cells.

The method for culturing primary gynecological tumor cells provided in the present invention comprises the following step: using the culture medium described above to conduct suspension culture of primary gynecological tumor cells.

In the above method, the primary gynecological tumor cells can be primary gynecological solid tumor cells or primary tumor cells in gynecological tumor pleural effusions and ascites samples.

When the primary gynecological tumor cells are primary gynecological solid tumor cells, the primary gynecological solid tumor cells can be obtained by dissociating gynecological solid tumor tissues with the sample dissociation solution described above.

Further, the sample dissociation solution can be used to dissociate gynecological solid tumor tissues according to a method comprising the following steps: according to the dosage of 0.1-0.3 mL (such as 0.1 mL) of the sample dissociation solution per mg of tissue, treating the chopped gynecological solid tumor tissue (for example, chopped into small pieces of 0.8-1.2 $mm^3$) with the sample dissociation solution preheated at 37° C. to conduct sample dissociation at 37° C. for 15 minutes to 3 hours. The dissociated sample is observed under a microscope every 15 minutes until a large number of single cells are observed.

When the primary gynecological tumor cells are the primary tumor cells in gynecological tumor pleural effusions and ascites samples, the primary tumor cells in gynecological tumor pleural effusions and ascites samples can be isolated from the gynecological tumor pleural effusions and ascites samples with the cell isolation buffer described above.

Further, the isolation buffer can be used to isolate the gynecological tumor pleural effusions and ascites samples according to a method comprising the following steps: suspending the cells in the gynecological tumor pleural effusions and ascites samples in the cell isolation buffer, and then obtaining the primary tumor cells in gynecological tumor pleural effusions and ascites samples by density gradient centrifugation (using Ficoll lymphocyte separation medium).

Further, before using the isolation buffer to isolate gynecological tumor pleural effusions and ascites samples, the method can further comprise a step of pre-treating the gynecological tumor pleural effusions and ascites samples: removing the impurities, clots and other components that affect cell density gradient separation in the gynecological tumor pleural effusions and ascites samples.

In the method, the primary gynecological tumor cell culture medium can be used to conduct the suspension culture of the primary gynecological tumor cells according to a method comprising the following steps: in a cell culture container M, suspending the primary gynecological tumor cells using the primary gynecological tumor cell culture medium and culturing the cells at 37° C. and 5% $CO_2$, and changing the culture medium every 2-4 days (such as 3 days) until the cells form clumps with a diameter of 80-120 μm (such as 100 μm).

In the method, the initial seeding density can be $10^5$ cells/$cm^2$ container bottom area, taking a six-well plate as an example, the cells can be plated at a density of $10^6$ cells per well.

In the method, the cell culture container M can be any one of the followings: (1) a cell culture container made of polystyrene, a cell culture container made of polycarbonate, a cell culture container made of polymethyl methacrylate, a cell culture container made of COC resin, a cell culture container made of cycloolefin polymer or a cell culture container with a low-attachment-surface, (11) a cell culture container obtained by modifying the cell culture container in (T) by CYTOP.

Further, the cell culture container is a cell culture dish, a cell culture well plate or a microwell plate chip for cell culture (such as the microwell plate chip shown in FIG. 5 in Example 15) and the like.

In (II), CYTOP modification can be performed on the cell culture container in (1) according to a method comprising the following steps: etching the cell culture container in (I) with pure oxygen for 3 minutes at a power of 20 W; then covering the surface of the cell culture container with the aforementioned 1% CYTOP solution, and drying 1% CYTOP solution, thereby completing the CYTOP modification.

Further, the method can further comprise the following step of treating the gynecological solid tumor tissue prior to dissociation: washing the surface of the gynecological solid tumor tissue sample with 70-75% (v/v) ethanol (such as 75% ethanol) for 10 to 30 seconds; washing the gynecological solid tumor tissue sample 10-20 times (such as 10 times) with the sample washing solution described above, and washing the gynecological solid tumor tissue sample with a sterile PBS solution 5-10 times (such as 5 times); then removing impurities, connective tissues, adipose tissues, necrotic tissues and other components in the gynecological solid tumor tissue sample that affect the primary cell culture.

The step of treating the gynecological solid tumor tissue prior to dissociation needs to be conducted on ice, and the entire operation step needs to be completed within 10 minutes.

Further, the gynecological solid tumor tissue sample subjected to the treatment prior to dissociation needs to be within 2 hours after excision, and it has been kept in the sample preservation solution described above before the treatment prior to dissociation is performed.

Further, in the method, after dissociating the gynecological solid tumor tissue with the sample dissociation solution, the following steps can be further comprised: terminating the dissociation reaction using 8-15 volumes (such as 10 volumes) of the aforementioned digestion stop solution, and collecting the cell suspension; filtering the cell suspension with a 100 μm or 40 μm sterile cell strainer to remove tissue debris and adherent cells; centrifuging at 800-1,000 g (such as 800 g) at room temperature for 10-15 minutes (such as 10 minutes), discarding the supernatant; then resuspending the cells in 3-5 mL (such as 5 mL) of sterile PBS; then centrifuging at 800-1,000 g (such as 800 g) at room temperature for 10-15 minutes (such as 10 minutes), discarding the supernatant; then resuspending the cell pellet in the primary gynecological solid tumor cell culture medium, observing the cell state under a microscope, and counting the cells.

Further, in the method, the following step can be further comprised: when the primary gynecological tumor cells form clumps with a diameter of 80-120 μm (such as 100 μm), the primary gynecological tumor cells are passaged.

Further, the digestion temperature when carrying out the cell passage is 37° C.

Further, the digestion stop solution used in the cell passage is the digestion stop solution described above.

More specifically, the steps of carrying out the cell passage comprise: collecting the cell clump to be passaged, washing the cell chump with sterile PBS solution after centrifugation, centrifuging again, and then resuspending the cell clump in the cell digestion solution, digest at 37° C. until the cell clump is digested into single cells, terminating the digestion reaction using the digestion stop solution (the amount is 5-10 volumes, such as 10 volumes), and collecting the cell suspension; resuspending the cell pellet in the primary gynecological tumor cell culture medium, counting, and then performing cell suspension culture in a culture container with a low-attachment-surface (the initial seeding density can be $10^5$ cells/cm$^2$ container bottom area, taking a 6-well plate as an example, the cells are plated at a density of $10^6$ cells per well) at 37° C. and 5% $CO_2$. All the centrifuging steps in the above-mentioned passaging steps can specifically be centrifuging at 800-1,000 g (such as 800 g) at room temperature for 10-20 minutes (such as 10 minutes).

Further, the method can further comprise the steps of cryopreserving and/or resuscitating the primary gynecological tumor cells after 2-3 passages and expansions.

In the method, the cell cryopreservation medium used in the cryopreservation is the cell cryopreservation medium described above.

Further, the specific steps of carrying out the cryopreservation comprise: collecting the cell clump to be cryopreserved, washing the cell clump with sterile PBS solution after centrifugation, centrifuging again, and then resuspending the cell clump in the cell digestion solution and digesting at 37° C. until the cell clump is digested into single cells, terminating the digestion reaction using the digestion stop solution (the amount is 5-10 volumes, such as 10 volumes), and collecting the cell suspension; after centrifugation, resuspending the cell pellet in the cell cryopreservation medium at a density of 0.5-2×$10^6$ cells/mL (such as $10^6$ cells/mL), cryopreserving the cells in a gradient cooling box overnight, and then transferring them to liquid nitrogen for long-term storage. All the centrifuging steps in the above-mentioned cryopreserving steps can specifically be centrifuging at 800-1,000 g (such as 800 g) at room temperature for 10-20 minutes (such as 10 minutes).

Further, the specific steps of carrying out the resuscitation: taking out a cryopreservation tube containing the cells to be resuscitated from the liquid nitrogen, rapidly thawing the cells in sterile water at 37-39° C. (such as 37° C.); after centrifugation (such as 800-1,000 g, e.g. centrifugation at 800 g at room temperature for 5-10 minutes, such as 10 minutes), resuspending the cell pellet in the primary gynecological tumor cell culture medium, and then performing cell suspension culture in a culture container with a low-attachment-surface (the initial seeding density can be $10^5$ cells/cm$^2$ container bottom area, resuscitating each tube of cells ($10^6$ cells) to a 3.5 cm culture dish at 37° C. and 5% $CO_2$.

In each of the above aspects, the primary gynecological tumor cells are isolated from surgical samples or puncture biopsy samples or pleural effusions and ascites samples (pleural effusions or ascites) of gynecological tumor patients. Among them, the gynecological solid tumor tissue samples obtained from surgical samples should preferably weigh more than 20 mg, the puncture biopsy samples (belonging to solid tumor samples) should be more than 4, and the pleural effusions and ascites samples should be more than 100 mL, In the present invention, all of the above PBS solutions can be 1×PBS, pH 7.3-7.5. The specific composition of 1×PBS is as follows: the solvent is water, the solutes and their concentrations are as follows: $KH_2PO_4$ 144 mg/L, NaCl 9,000 mg/L, $Na_2HPO_4.7H_2O$ 795 mg/L.

DESCRIPTION OF THE DRAWINGS

FIG. 2A shows the result in culture medium A; panel FIG. 2B shows the result in culture medium B.

FIG. 3A shows the result in culture medium A; panel FIG. 3B shows the result in culture medium B.

FIG. 4A shows the result in culture medium A; panel FIG. 4B shows the result in culture medium B.

DETAILED DESCRIPTION OF THE INVENTION

Figure 1A:
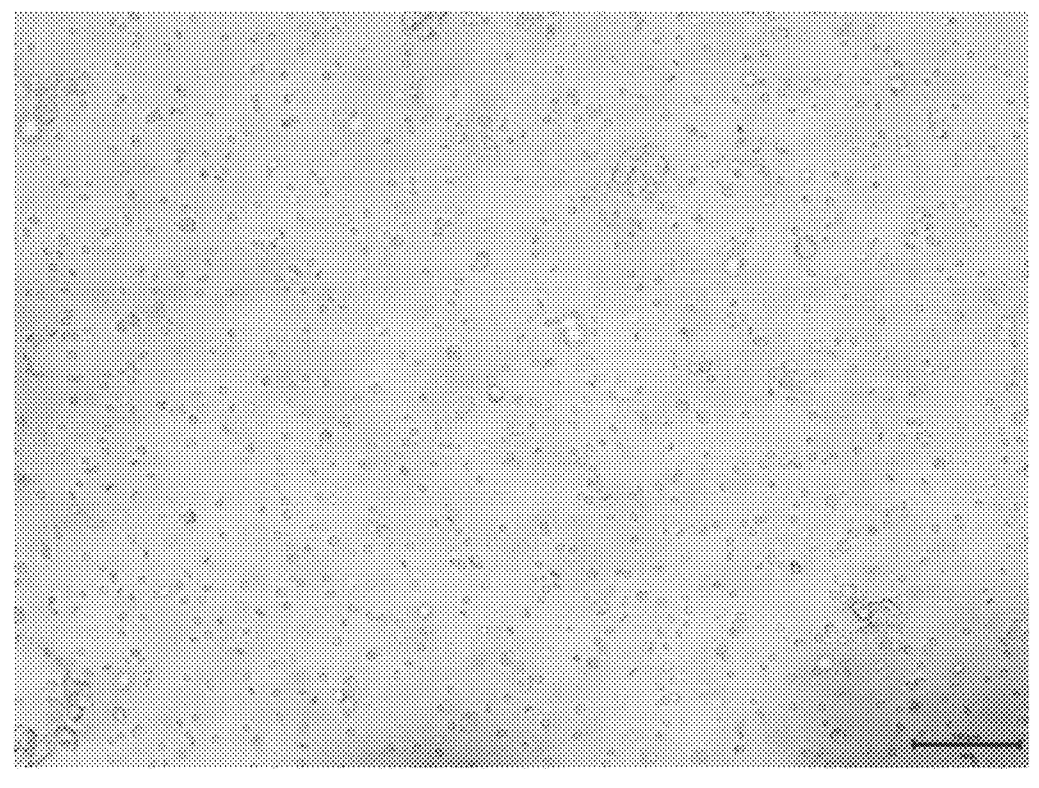
FIGS. 1A and 1B shows single cells obtained from breast cancer tissues after treatment. Scale bar=100 μm for 100× magnification. Panels FIG. A and FIG. 1B are two parallel processing results, respectively.

The following examples facilitate a better understanding of the present invention, but do not limit the present invention. The experimental methods in the following examples are conventional methods unless otherwise specified. The test materials used in the following examples are commercially available unless otherwise specified. The quantitative tests in the following examples are performed in triplicate, and the results are averaged.

Example 1: Preparation of Reagents for Culturing Primary Gynecological Tumor Cells 1. Sample Preservation Solution (100 mL)

The specific formulation of the sample preservation solution (100 mL) is shown in Table 1.

TABLE 1

| Sample preservation solution (100 mL) | | | |
|---|---|---|---|
| Reagent | Article number | Amount | Final concentration |
| Fetal bovine serum | Gibco#16000-044 | 2 mL | 2% |
| Two antibiotics P/S | Gibco#15140122 | 1 mL | 1% |
| HEPES | Gibco#15630080 | 1 mL | 10 mM |
| HBSS | Gibco#14170161 | To 100 mL | |

After preparation, the sample preservation solution was sub-packaged in 15 mL centrifuge tubes, 5 mL/tube. After sub-packaging, it can be stored at 4° C. for 1 month.

2. Sample Washing Solution (100 mL)

The specific formulation of the sample washing solution (100 mL) is shown in Table 2.

TABLE 2

| Sample washing solution (100 mL) | | | |
|---|---|---|---|
| Reagent | Article number | Amount | Final concentration |
| Two antibiotics P/S | Gibco#15140122 | 1 mL | 1% |
| PBS | Gibco#21-040-CVR | To 100 mL | |

The sample washing solution should be prepared just before use.

3. Sample Dissociation Solution (10 mL)

The specific formulation of the sample dissociation solution (10 mL) is shown in Table 3.

TABLE 3

| Sample dissociation solution (10 mL) | | | |
|---|---|---|---|
| Reagent | Article number | Amount | Final concentration |
| 10× Collagenase I | 10× stock solution | 1 mL | 200 U/mL |
| 10× Collagenase III | 10× stock solution | 1 mL | 290 U/mL |
| 10× Collagenase IV | 10× stock solution | 1 mL | 200 U/mL |
| PBS | Gibco#21-040-CVR | To 10 mL | |

Note:
the sample dissociation solution should be prepared just before use. In Table 3, the preparations of the collagenase stock solutions are shown in Tables 4-6.

TABLE 4

| 10× Collagenase I stock solution (100 mL) | | | |
|---|---|---|---|
| Reagent | Article number | Amount | Final concentration |
| Collagenase I | Gibco#17100-017 | 1 g | 2,000 U/mL |
| PBS | Gibco#21-040-CVR | To 100 mL | |

After preparation, 10×Collagenase I stock solution was sub-packaged in 1.5 mL sterile centrifuge tubes, 1 mL/tube. This stock solution can be stored for a long time at −20° C.

TABLE 5

| 10× Collagenase III stock solution (100 mL) | | | |
|---|---|---|---|
| Reagent | Article number | Amount | Final concentration |
| Collagenase III | Solarbio#C8490 | 1 g | 2,900 U/mL |
| PBS | Gibco#21-040-CVR | To 100 mL | |

After preparation, 10×Collagenase III stock solution was sub-packaged in 1.5 mL sterile centrifuge tubes, 1 mL/tube. This stock solution can be stored for a long time at −20° C.

TABLE 6

| 10× Collagenase IV stock solution (100 mL) | | | |
|---|---|---|---|
| Reagent | Article number | Amount | Final concentration |
| Collagenase IV | Gibco#17104-019 | 1 g | 2,000 U/mL |
| PBS | Gibco#21-040-CVR | To 100 mL | |

After preparation, 10×Collagenase IV stock solution was sub-packaged in 1.5 mL sterile centrifuge tubes, 1 mL/tube. This stock solution can be stored for a long time at −20° C.

In Tables 4 to 6, the unit U of collagenase (collagenase I, collagenase III or collagenase IV) is defined by the enzymatic activity of the protease: when the collagenase (collagenase I, collagenase III or collagenase IV) is treated with 1 U of the protease for 5 hours at pH 7.5, 37° C., 1 μmol of L-leucine can be released.

4. Cell Digestion Solution (10 mL)

The specific formulation of the cell digestion solution (10 mL) is shown in Table 7.

TABLE 7

| Cell digestion solution (10 mL) | | | |
|---|---|---|---|
| Reagent | Article number | Amount | Final concentration |
| Accutase | Gibco#A11105-01 | 5 mL | 5 mM |
| 0.5M EDTA | Invitrogen#AM9261 | 10 μL | |
| TrypLE Express | Gibco#12604013 | 2 mL | |
| PBS | Gibco#21-040-CVR | To 10 mL | |

The cell digestion solution should be prepared just before use.

5. Digestion stop solution (100 mL)

The specific formulation of the digestion stop solution (100 mL) is shown in Table 8.

TABLE 8

| Digestion stop solution (100 mL) | | | |
|---|---|---|---|
| Reagent | Article number | Amount | Final concentration |
| Fetal bovine serum | Gibco#16000-044 | 10 mL | 10% |
| Two antibiotics P/S | Gibco#15140122 | 1 mL | 1% |
| DMEM medium | Gibco#l1965-092 | To 10 mL | |

After preparation, the digestion stop solution can be stored at 4° C. for 1 month.

6. Primary Gynecological Tumor Cell Culture Medium (100 mL)

There are two types of primary gynecological tumor cell culture medium (100 mL), designated as culture medium A and culture medium B. The specific formulation of culture medium A is shown in Table 9. The specific formulation of culture medium B is shown in Table 10.

TABLE 9

| Primary gynecological tumor cell culture medium A (100 mL) | | | |
|---|---|---|---|
| Reagent | Article number | Amount | Final concentration |
| Solution containing three antibiotic and antimycotic agents | Gibco#15240062 | 1 mL | 1% |
| HEPES | Gibco#15630080 | 1 mL | 10 mM |
| GlutaMax | Gibco#35050061 | 1 mL | 1% |
| 1,000× Human recombinant protein EGF | 1,000× stock solution | 50-500 μL | 10-100 ng/mL |
| 1,000× Human recombinant protein bFGF | 1,000× stock solution | 50-250 μL | 10-50 ng/mL |
| 1,000× Human recombinant protein HGF | 1,000× stock solution | 25-125 μL | 5-25 ng/mL |
| 1,000× Human recombinant protein MSP | 1,000× stock solution | 25-125 μL | 5-25 ng/mL |
| Hydrocortisone | 1,000× stock solution | 20-200 μL | 1-10 μg/mL |
| N-2 Supplement | Gibco#17502001 | 1 mL | 1% |
| 1,000× Y-27632 | 1,000× stock solution | 50-200 μL | 5-20 μM |
| Progesterone | 100,000× stock solution | 5-10 μL | 50-100 nM |
| β-Estradiol | 100,000× stock solution | 1-5 μL | 10-50 nM |
| Advanced DMEM/F12 medium | Gibco#12634010 | To 100 mL | |

TABLE 9

| Primary gynecological tumor cell culture medium B (100 mL) | | | |
|---|---|---|---|
| Reagent | Article number | Amount | Final concentration |
| Solution containing three antibiotic and antimycotic agents | Gibco#15240062 | 1 mL | 1% |
| HEPES | Gibco#15630080 | 1 mL | 10 mM |
| GlutaMax | Gibco#35050061 | 1 mL | 1% |
| 1,000× Human recombinant protein EGF | 1,000× stock solution | 50-500 μL | 10-100 ng/mL |
| 1,000× Human recombinant protein bFGF | 1,000× stock solution | 50-250 μL | 10-50 ng/mL |
| 1,000× Human recombinant protein HGF | 1,000× stock solution | 25-125 μL | 5-25 ng/mL |
| 1,000× Human recombinant protein MSP | 1,000× stock solution | 25-125 μL | 5-25 ng/mL |
| N-acetyl-L-cysteine | 1,000× stock solution | 100-400 μL | 0.5-2 mM |
| N-2 Supplement | Gibco#17502001 | 1 mL | 1% |
| l,000× Y-27632 | 1,000× stock solution | 50-200 μL | 5-20 μM |
| Progesterone | 100,000× stock solution | 5-10 μL | 50-100 nM |
| β-Estradiol | 100,000× stock solution | 1-5 μL | 10-50 nM |
| Advanced DMEM/F12 medium | Gibco#12634010 | To 100 mL | |

After preparation, the primary gynecological tumor cell culture media need to be filtered and sterilized with a 0.22 μM syringe filter (Millipore LGP033RS), and can be stored at 4° C. for two weeks.

In Table 9 and Table 10, the preparations of human recombinant protein stock solutions are shown in Tables 12-15, the preparation of hydrocortisone stock solution is shown in Table 16, the preparation of N-acetyl-L-cysteine stock solution is shown in Table 17, the preparation of Y-27632 stock solution is shown in Table 18, the preparation of progesterone stock solution is shown in Table 19, the preparation of β-estradiol stock solution is shown in Table 20. 100×BSA solution formulation required to prepare these stock solutions is shown in Table 11.

TABLE 11

100 × BSA solution (1 mL)

| Reagent | Article number | Amount | Final concentration |
|---|---|---|---|
| BSA | Sigma#A1933 | 0.1 g | 0.1 g/mL |
| PBS | Gibco#21-040-CVR | To 1 mL | |

100 × BSA solution should be prepared just before use.

TABLE 12

1,000× Human recombinant protein EGF stock solution (5 mL)

| Reagent | Article number | Amount | Final concentration |
|---|---|---|---|
| Human recombinant protein EGF | Peprotech AF-100-15-100 | 100 μg | 20 ug/mL |
| 100× BSA solution | | 500 μL | 0.01 g/mL |
| PBS | Gibco#21-040-CVR | To 5 mL | |

After preparation, 1,000×human recombinant protein EGF stock solution was sub-packaged in 1.5 mL sterile centrifuge tubes. This solution can be stored for a long term at −80° C.

TABLE 13

1,000 × Human recombinant protein bFGF stock solution (2.5 mL)

| Reagent | Article number | Amount | Final concentration |
|---|---|---|---|
| Human recombinant protein bFGF | Peprotech AF-100-18B-50 | 50 μg | 20 μg/mL |
| 100 × BSA solution | | 250 μL | 0.01 g/mL |
| PBS | Gibco#21-040-CVR | To 2.5 mL | |

After preparation, 1,000×human recombinant protein bFGF stock solution was sub-packaged in 1.5 mL sterile centrifuge tubes. This solution can be stored for a long term at −80° C.

TABLE 14

1,000 × Human recombinant protein HGF stock solution (5 mL)

| Reagent | Article number | Amount | Final concentration |
|---|---|---|---|
| Human recombinant protein HGF | Peprotech AF-100-39-100 | 100 μg | 20 μg/mL |
| 100 × BSA solution | | 500 μL | 0.01 g/mL |
| PBS | Gibco#21-040-CVR | To 5 mL | |

After preparation, 1,000×human recombinant protein HGF stock solution was sub-packaged in 1.5 mL sterile centrifuge tubes. This solution can be stored for a long term at −80° C.

TABLE 15

1,000 × Human recombinant protein MSP stock solution (2.5 mL)

| Reagent | Article number | Amount | Final concentration |
|---|---|---|---|
| Human recombinant protein MSP | R&D#352-MS-050 | 50 μg | 20 μg/mL |
| 100 × BSA solution | | 250 μL | 0.01 g/mL |
| PBS | Gibco#21-040-CVR | To 2.5 mL | |

After preparation, 1,000×human recombinant protein MSP stock solution was sub-packaged in 1.5 mL sterile centrifuge tubes. This solution can be stored for a long term at −80° C.

TABLE 16

1,000 × Hydrocortisone stock solution (10 mL)

| Reagent | Article number | Amount | Final concentration |
|---|---|---|---|
| Hydrocortisone | Selleck#S1696 | 50 mg | 5 mg/mL |
| DMSO | Sigma#D2438 | To 10 mL | |

After preparation, 1,000×N-acetyl-L-cysteine stock solution was sub-packaged in 0.5 mL sterile centrifuge tubes. This solution can be stored for a long term at −20° C.

TABLE 17

1,000 × N-acetyl-L-cysteine stock solution (5 mL)

| Reagent | Article number | Amount | Final concentration |
|---|---|---|---|
| N-acetyl-L-cysteine | Sigma#A9165 | 0.41 g | 0.5 M |
| Ultrapure water | | To 5 mL | |

After preparation, 1,000×N-acetyl-L-cysteine stock solution was sub-packaged in 0.5 mL sterile centrifuge tubes. This solution can be stored for a long term at −20° C.

TABLE 18

| 1,000 × Y-27632 stock solution (3.125 mL) | | | |
|---|---|---|---|
| Reagent | Article number | Amount | Final concentration |
| Y-27632 | MCE#129830-38-2 | 10 mg | 10 mM |
| Ultrapure water | | To 3.125 mL | |

After preparation, 1,000×Y-27632 stock solution was sub-packaged in 0.5 mL sterile centrifuge tubes. This solution can be stored for a long term at −20° C.

TABLE 19

| 100,000 × Progesterone stock solution (15.9 mL) | | | |
|---|---|---|---|
| Reagent | Article number | Amount | Final concentration |
| Progesterone | Sigma#V900699 | 5 mg | 1 mM |
| Absolute ethanol | | To 15.9 mL | |

After preparation, 100,000×progesterone stock solution was sub-packaged in 0.5 mL sterile centrifuge tubes. This solution can be stored for a long term at −20° C.

TABLE 20

| 10,000 × β-Estradiol stock solution (18.36 mL) | | | |
|---|---|---|---|
| Reagent | Article number | Amount | Final concentration |
| β-Estradiol | Sigma#E2758 | 5 mg | 1 mM |
| Absolute ethanol | | To 18.36 mL | |

After preparation, 10,000×β-Estradiol stock solution was sub-packaged in 0.5 mL sterile centrifuge tubes. This solution can be stored for a long term at −20° C.

7. Cell Cryopreservation Medium

The specific formulation of cell cryopreservation medium is shown in Table 21.

TABLE 21

| Cell cryopreservation medium | | |
|---|---|---|
| Reagent | Article number | Amount |
| Advanced DMEM/F12 medium | Gibco#12634010 | 20 mL |
| DMSO | Sigma#D2438 | 2 mL |
| 1% methyl cellulose solution | | 1 mL |

The cell cryopreservation medium should be prepared just before use.

In Table 21, the preparation of 1% methylcellulose solution is shown in Table 22.

TABLE 22

| 1% Methylcellulose solution (10 mL) | | | |
|---|---|---|---|
| Reagent | Article number | Amount | Final concentration |
| Methyl cellulose | Sigma#M7027 | 0.1 g | 10 g/L |
| Ultrapure water | | To 10 mL | |

After preparation, 1% methylcellulose solution can be stored for a long term at 4° C.

8. 1% CYTOP Solution

TABLE 23

| 1% CYTOP solution (100 mL) | | | |
|---|---|---|---|
| Reagent | Article number | Amount | Final concentration |
| CYTOP | Asashi glass#CTL-809M | 1 mL | 1% |
| Fluorine oil | 3M# FC40 | To 100 mL | |

After preparation, 1% CYTOP solution can be stored for a long term at room temperature.

9. Cell Isolation Buffer (100 mL)

The specific formulation of cell isolation buffer (100 mL) is shown in Table 24.

TABLE 24

| Cell isolation buffer (100 mL) | | | |
|---|---|---|---|
| Reagent | Article number | Amount | Final concentration |
| Two antibiotics P/S | Gibco#15140122 | 1 mL | 1% |
| heparin sodium solution | 1,000 × stock solution | 1 mL | 10 IU/mL |
| PBS | Gibco#21-040-CVR | To 100 mL | |

After preparation, the cell isolation buffer can be stored at 4° C. for 1 month.

In Table 24, the preparation of heparin sodium solution is shown in Table 25.

TABLE 25

| 1,000 × Heparin sodium (1 mL) | | | |
|---|---|---|---|
| Reagent | Article number | Amount | Final concentration |
| Heparin sodium | Solarbio#H8270 | 10 kIU | 10 IU/L |
| Ultrapure water | | To 1 mL | |

1,000×Heparin sodium should be prepared just before use.

Example 2: Acquisition of Postoperative Specimens/Biopsy Puncture Specimens/Pleural Effusions and Ascites Samples of Gynecological Tumor 1. This study was conducted by cooperating with a 3a grade hospital, and passed a formal medical ethics review.

2. The attending physician selected the patients enrolled according to the clinical indications stipulated in the medical guidelines, and selected appropriate samples for in vitro culture according to the intraoperative clinical indications. The selection criteria for the samples were: primary breast cancer, ovarian cancer, endometrial cancer, cervical cancer or the metastatic lesions thereof, surgical specimens weighing more than 20 mg, or pleural effusions and ascites samples exceeding 100 mL, or puncture biopsy specimens exceeding 4.

3. The attending physician provided basic clinical information such as gender, age, medical history, family history, smoking history, pathological staging, and clinical diagnosis of each patient. The patient's name, ID number and other information related to the patient's privacy were hidden and replaced with a unified experimental number. The naming principle of the experimental number is the eight-digit date of the sample collection+the last four digits of the patient's hospitalization number. For example, for the sample provided on Jan. 1, 2018, the patient's hospitalization number was T001512765, then the sample experiment number was 201801012765.

4. During the operation, the surgeon collected fresh postoperative specimens/biopsy puncture specimens in the sterile environment of the operating room, and placed them in the prepared sample preservation solution (see Example 1). The samples were temporarily stored on ice after excision, and transported to the laboratory within two hours for further operations. The pleural effusions and ascites samples were transported to the laboratory within 48 hours for further operations.

Example 3. Treatment of Gynecological Solid Tumor Tissue Samples Before Dissociation The following operations need to be performed on ice, and the whole experiment needs to be completed within 10 minutes.

The surgical equipment used in the following operations must be sterilized by high temperature and high pressure in advance, and can be used after drying.

1. Weigh the sample.
2. Wash the surface of the sample with 75% (v/v) ethanol for 10 to 30 seconds.
3. Wash the sample 5 times with the sample washing solution and 5 times with sterile PBS solution.
4. Use ophthalmic scissors, ophthalmic forceps, scalpel and other equipment to carefully peel off the adipose tissue, connective tissue and necrotic tissue in the sample.

Example 4. Dissociation of Gynecological Solid Tumor Tissue Samples

The surgical equipment used in this example all need to be sterilized by high temperature and high pressure in advance, and can be used after drying.

1. Use ophthalmic scissors to cut the tissue into small pieces of about 1 $mm^3$.
2. According to the dosage of 0.1 mL of the sample dissociation solution (see Example 1) per mg of tissue, treat the chopped tissue sample with the sample dissociation solution preheated at 37° C. to conduct sample dissociation at 37° C. for 15 minutes to 3 hours. Observe the dissociated sample under a microscope every 15 minutes until a large number of single cells can be observed.
3. Terminate the dissociation reaction using 10 volumes of the digestion stop solution (see Example 1), and collect the cell suspension.
4. Filter the cell suspension with a 100 μm sterile cell strainer to remove tissue debris and adherent cells.
5. Centrifuge at 800 g at room temperature for 10 minutes and discard the supernatant.
6. Resuspend the cells in 5 mL of sterile PBS, centrifuge at 800 g for 10 minutes at room temperature, and discard the supernatant.
7. Resuspend the cell pellet in the primary gynecological tumor cell culture medium (see Example 1), observe the cell state under a microscope, and count the cells.

Figure 1B:
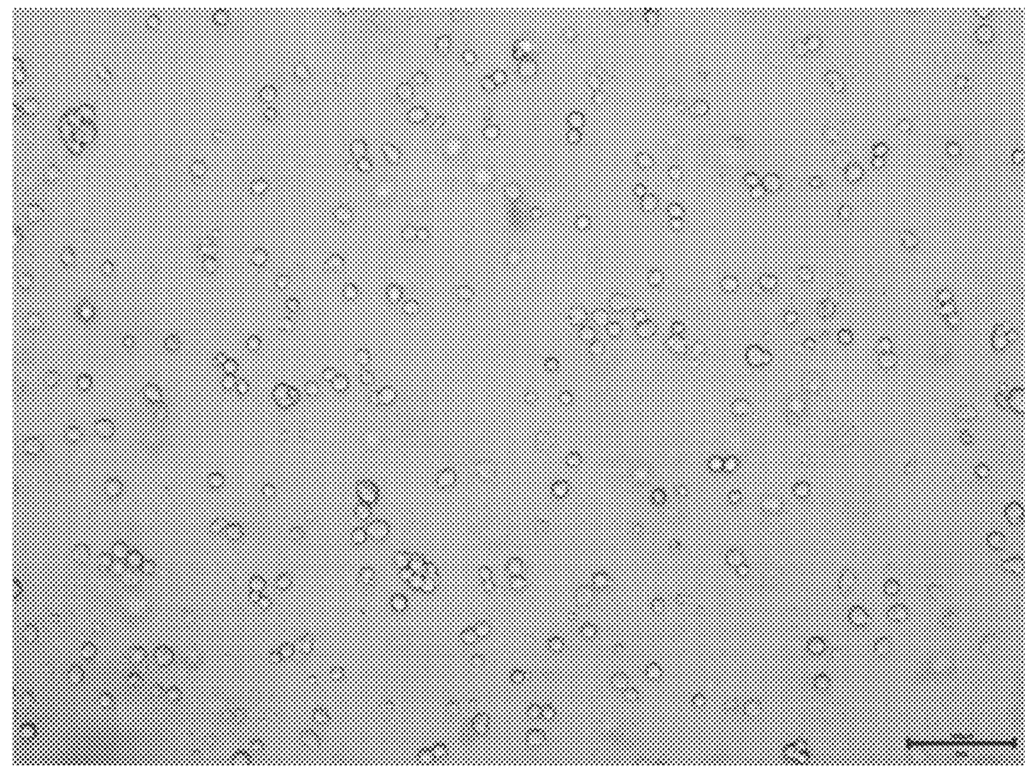

As shown in FIG. 1, in the dissociated single cell suspension, in addition to tumor cells, a large number of other types of cells, such as erythrocytes, lymphocytes, fibroblasts, etc., are contained. One of the advantages of this method is that in the subsequent culture process, only cancer cells were expanded in large quantities, while the proportion of other cells gradually decreased or even disappeared, and finally primary gynecological tumor cells with higher purity were obtained.

Example 5. Pretreatment of Gynecological Tumor Pleural Effusions and Ascites Samples The following operations need to be performed on ice, and the whole experiment needs to be completed within 10 minutes.

1. Allow the gynecological tumor pleural effusions and ascites sample to stand on ice for about 30 minutes, so that the blood clots and large insoluble solids in the sample settle to the bottom of the sample tube.
2. Carefully transfer the supernatant to a 50 mL sterile centrifuge tube, and add one volume of pre-cooled PBS and mix well.
3. Centrifuge at 2,000 g for 5 minutes at 4° C. and discard the supernatant.
4. Resuspend the cell pellet in the cell isolation buffer (see Example 1), centrifuge at 2,000 g for 5 minutes at 4° C., and discard the supernatant.
5. Resuspend the cell pellet in the cell isolation buffer (see Example 1), and adjust the cell concentration to $10^7$/mL.

Example 6. Density Gradient Centrifugation of Gynecological Tumor Pleural Effusions and Ascites Samples 1. Add the same volume of Ficoll cell isolation solution (MP #50494) as the cell suspension to a 50 mL sterile centrifuge tube.
2. Carefully add the cell suspension to the upper layer of the cell isolation solution so that a clear interface is formed between the two.
3. Centrifuge at 2,000 g horizontally at room temperature for 20 minutes.
4. Transfer the middle white film layer to a new tube.
5. Resuspend the cell pellet in 20 mL of sterile PBS, centrifuge at 1,500 g for 10 minutes at room temperature, and discard the supernatant.
6. Resuspend the cell pellet in primary gynecological tumor cell culture medium (see Example 1), observe the cell state under a microscope, and count the cells.

The results showed that in the isolated single cell suspension, in addition to tumor cells, a large number of other types of cells, such as erythrocytes, lymphocytes, fibroblasts, etc., are contained. One of the advantages of this method is that in the subsequent culture process, only cancer cells were expanded in large quantities, while the proportion of other cells gradually decreased or even disappeared, and finally primary gynecological tumor cells with higher purity were obtained.

Example 7. Primary Gynecological Tumor Cell Culture

1. Use a low-attachment-surface for suspension culture of primary gynecological tumor cells, and the culture medium used is the primary gynecological tumor cell culture medium A or culture medium B in Example 1; Take a six-well plate as an example, plate at a density of $10^6$ cells per well, and culture in a cell incubator at 37° C. and 5% $CO_2$.

When the culture medium is culture medium A, the final concentration of human recombinant protein EGF is 50 ng/mL; the final concentration of human recombinant protein bFGF is 20 ng/mL; the final concentration of human recombinant protein HGF is 20 ng/mL; the final concentration of human recombinant protein MSP is 20 ng/mL; the final concentration of hydrocortisone is 10 μg/mL; the final concentration of Y-27632 is 10 μM; the final concentration of progesterone is 100 nM; and the final concentration of β-estradiol is 10 nM.

When the culture medium is culture medium B, the final concentration of human recombinant protein EGF is 50 ng/mL; the final concentration of human recombinant protein bFGF is 20 ng/mL; the final concentration of human recombinant protein MSP is 20 ng/mL; the final concentration of recombinant protein MSP is 20 ng/mL; the final concentration of N-acetyl-L-cysteine is 1 mM; the final concentration of Y-27632 is 10 μM; the final concentration of progesterone is 100 nM; and the final concentration of 3-estradiol is 10 nM.

2. Observe the cell state every day, and change the culture medium every 3 days until the cells form clumps with a diameter of about 100 μm.

Figure 2A:
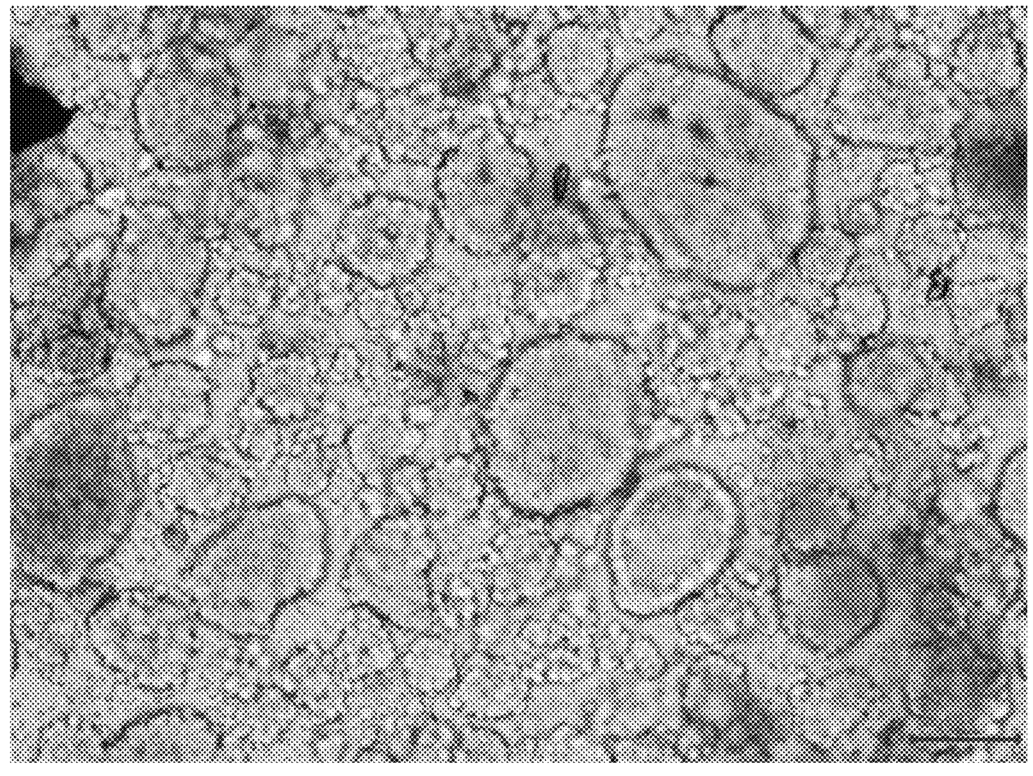
FIGS. 2A and 2B shows the cell clumps obtained after primary culture of a breast cancer tissue. Scale bar=100 μm for 100×magnification. Panel
Figure 2B:
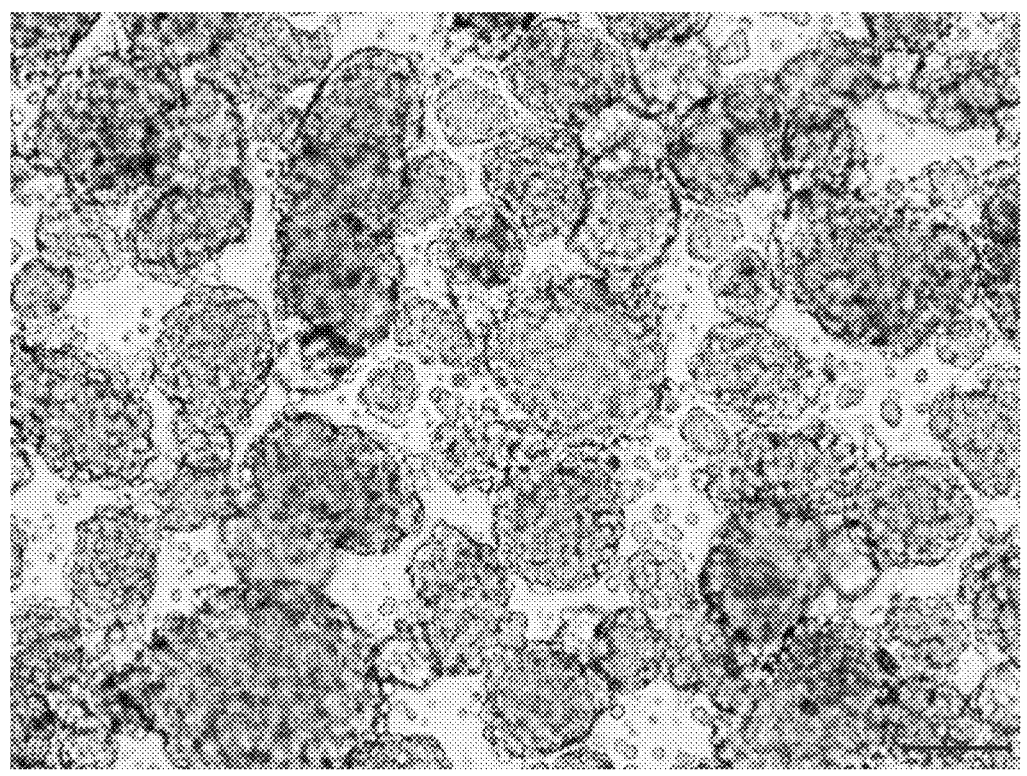

As shown in FIG. 2, after 3-10 days of culture, the tumor cells were massively expanded to form cell clumps with a diameter of 100 μm, the total number of tumor cells could exceed $10^7$, and the number of other types of cells was significantly reduced or even disappeared. This method has been tested on a large number of samples, and the success rate of in vitro culture of primary gynecological tumor cells can reach 70%.

Example 8. Primary Gynecological Tumor Cell Passage

1. Collect the cell clump in the culture dish, centrifuge at 800 g for 10 minutes at room temperature, and discard the supernatant.

2. Wash the cell clump with sterile PBS solution, centrifuge at 800 g at room temperature for 10 minutes, and discard the supernatant.

3. Resuspend the cell pellet in the cell digestion solution (see Example 1) and digest at 37° C.; observe the digestion of the cell clump under a microscope every 5 minutes until the cell clump is all digested into single cells.

4. Terminate the dissociation reaction using 10 volumes of the digestion stop solution, and collect the cell suspension.

5. Centrifuge at 800 g at room temperature for 10 minutes and discard the supernatant.

6. Resuspend the cell pellet in the primary gynecological tumor cell culture medium (see Example 1), and count the cells.

7. Use a low-attachment-surface for primary gynecological tumor cell culture, and the medium used is the primary gynecological tumor cell culture medium in Example 1. Taking a six-well plate as an example, plate at a density of $10^6$ cells per well, and culture in a cell incubator at 37° C. and 5% $CO_2$.

Example 9. Cryopreservation of Primary Gynecological Tumor Cells

Primary gynecological tumor cells in suspension culture can be cryopreserved after 2-3 passages and expansions:

1. Collect the cell clump in the culture dish, centrifuge at 800 g for 10 minutes at room temperature, and discard the supernatant.

2. Wash the cell pellet with sterile PBS solution, centrifuge at 800 g at room temperature for 10 minutes, and discard the supernatant.

3. Resuspend the cell pellet in the cell digestion solution (see Example 1) and digest at 37° C.; observe the digestion of the cell clump under a microscope every 15 minutes until the cell clump is all digested into single cells.

4. Terminate the dissociation reaction using 10 volumes of the digestion stop solution, collect the cell suspension and count the cells.

5. Centrifuge at 800 g at room temperature for 10 minutes and discard the supernatant.

6. Resuspend the cell pellet in the cell cryopreservation medium (see Example 1) at a density of $10^6$ cells/mL, sub-package the cell suspension in 2 mL cryopreservation tubes, 1 mL/tube; cryopreserve the cells in a gradient cooling box overnight, and then transfer them to liquid nitrogen for long-term storage.

Example 10. Resuscitation of Primary Gynecological Tumor Cells

Primary gynecological tumor cells preserved in liquid nitrogen can be resuscitated:

1. Prepare sterile water at 37° C. five minutes in advance.

2. Remove the cell cryopreservation tube from the liquid nitrogen, and rapidly thaw the cells in sterile water at 37° C.

3. Centrifuge at 800 g for 10 minutes at room temperature and discard the supernatant.

4. Resuspend the cell pellet in the primary gynecological tumor cell culture medium (see Example 1), and use a low-attachment-surface for primary gynecological tumor cell culture; resuscitate each tube of cells to a 3.5 cm culture dish and culture in a cell incubator at 37° C. and 5% $CO_2$.

Example 11. HE Staining Identification of Primary Gynecological Tumor Cells

Description of the reagents and materials used in this example:

HE staining kit (Beijing Solarbio Biotechnology Co., Ltd., #G1120);

Cationic anti-off slides (Beijing Zhongshan Gold Bridge Biotechnology Co., Ltd.);

Xylene, methanol, acetone (Beijing Chemical Reagent Company, analytically pure);

Neutral balsam (Beijing Yili Fine Chemicals Co., Ltd.).

1. Make the suspended cells into a cell suspension with a concentration of $10^4$ cells/mL, add, dropwise, 10 μL to the cationic anti-off slide, and dry naturally.

2. Add, dropwise and with caution, 50 μL of methanol/acetone mixture (volume ratio 1:1) pre-cooled at 4° C. on the air-dried cells, and then place the slide in a 4° C. refrigerator to fix 10 mins.

3. Take out the slide with fixed cells and allow it to dry naturally at room temperature.

4. Wash the slide twice with 200 μL PBS.

5. When the water on the slide is slightly dry, add 100 μL of hematoxylin staining solution for 1 min.

6. Drain the hematoxylin staining solution and wash the slide 3 times with 200 μL of tap water.

7. Add, dropwise, 100 μL of differentiation solution to differentiate 1 min.

8. Drain the differentiation solution, wash the slide twice with tap water and once with distilled water.

9. Drain the water on the surface of the slide, add 200 μL of eosin staining solution dropwise for 40 s.

10. Drain the eosin staining solution, rinse with 75%, 80%, 90%, and 100% ethanol for 20 s, 20 s, 40 s, and 40 s.

11. After the ethanol is dry, add, dropwise 50 μL of xylene to permeabilize the cells.

12. After the xylene is completely dried, add a drop of neutral balsam dropwise, cover the slide with a coverslip, observe and take pictures under a microscope.

Figure 3A:
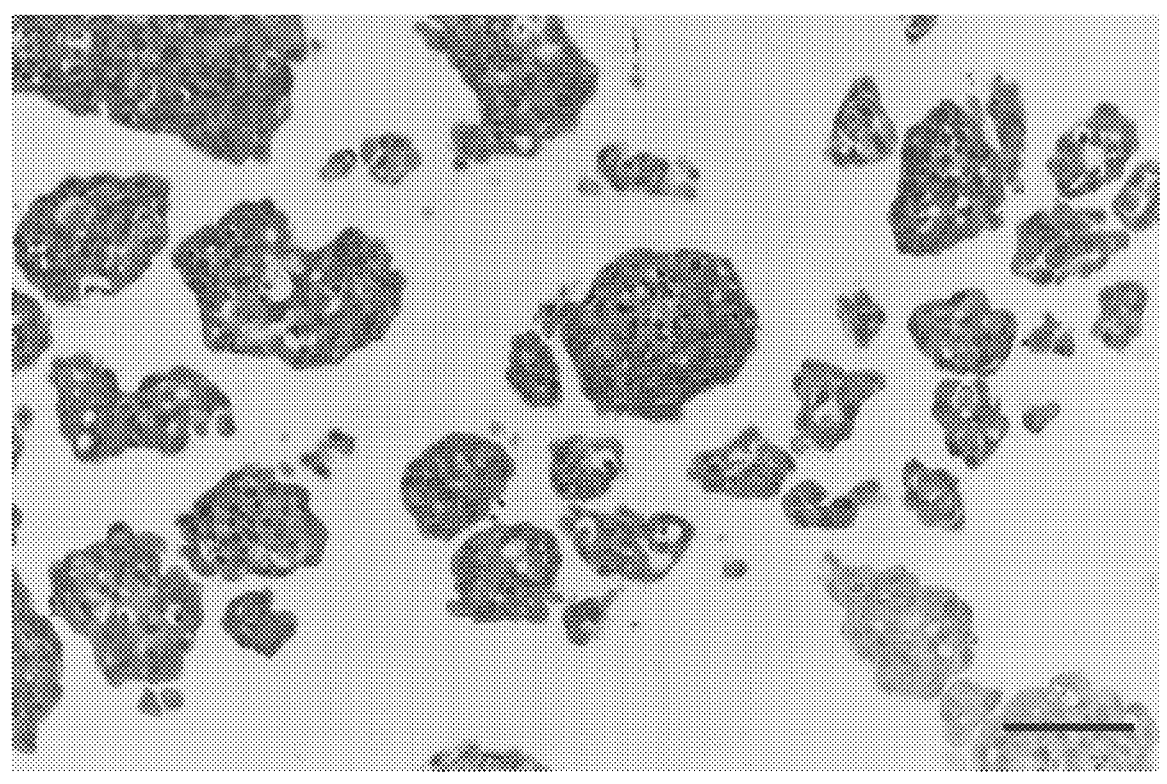
FIGS. 3A and 3B shows the HE staining results of gynecological tumor cells obtained after primary culture of a breast cancer tissue. Scale bar=100 μm for 200×magnification. Panel
Figure 3B:
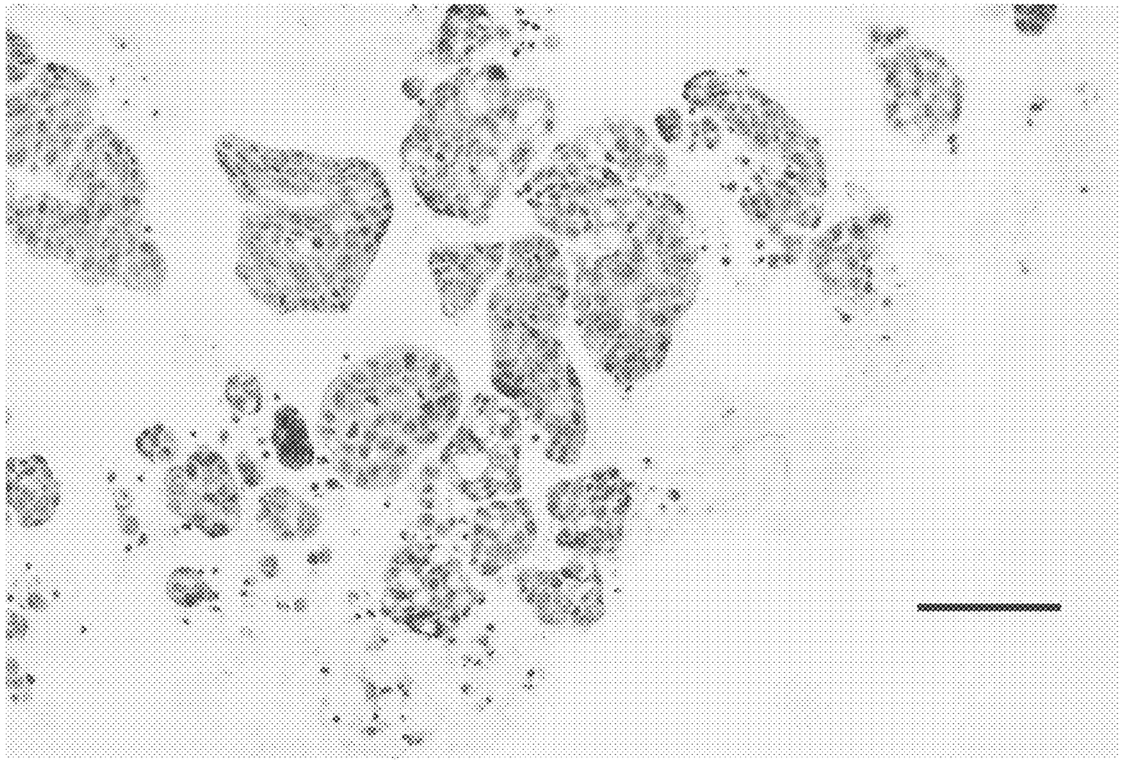

FIG. 3 shows the HE staining results of primary gynecological tumor cells cultured in vitro. It can be seen that these cells generally have tumor cells with high nuclear to cytoplasmic ratio, nuclear hyperchromatic, intranuclear chromatin condensation, multi-nucleus, and uneven cell size and other tumor cell features.

Example 12. Identification of Primary Gynecological Tumor Cells by Immunohistochemical Staining Description of reagents used in this example:

Paraformaldehyde (Beijing Chemical Reagent Company, analytically pure), 4% (4 g/100 mL) paraformaldehyde solution was prepared by dissolving paraformaldehyde powder in ultrapure water;

Hydrogen peroxide (Beijing Chemical Reagent Company, 35%);

Normal goat serum for blocking (Solarbio, SL038);

Immunohistochemical primary antibody (Fujian Maixin, kit-0012);

Immunohistochemical secondary antibody (Abcam, ab205719);

EDTA retrieval solution (Abcam, ab93684);

DAB color developing solution (SignalStain@ DAB Substrate Kit, 8059S)

Test medium: the two primary gynecological tumor cell culture media in Example 1, namely culture medium A or culture medium B.

When the culture medium is culture medium A, the final concentration of human recombinant protein EGF is 50 ng/mL; the final concentration of human recombinant protein bFGF is 20 ng/ml; the final concentration of human recombinant protein HGF is 20 ng/mL; the final concentration of human recombinant protein MSP is 20 ng/mL; the final concentration of hydrocortisone is 10 μg/mL; the final concentration of Y-27632 is 10 μM; the final concentration of progesterone is 100 nM; the final concentration of β-estradiol is 10 nM.

When the culture medium is culture medium B, the final concentration of human recombinant protein EGF is 50 ng/mL; the final concentration of human recombinant protein bFGF is 20 ng/ml; the final concentration of human recombinant protein HGF is 20 ng/mL; the final concentration of recombinant protein MSP is 20 ng/mL; the final concentration of N-acetyl-L-cysteine is 1 mM; the final concentration of Y-27632 is 10 μM; the final concentration of progesterone is 100 nM; the final concentration of β-estradiol is 10 nM.

The gynecological tumor cell clumps obtained by using the primary gynecological tumor cell culture media in Example 1 were collected for paraffin sectioning.

Protocol:

1. Soak sections in xylene I for 10 min and then xylene 11 for 10 min.

2. Soak in absolute ethanol I (5 min)—absolute ethanol II (5 min)—95% ethanol (5 min)—80% ethanol (5 min)—70% ethanol (5 min), then rinse with deionized water 2 times, 2 min each time.

3. Put the tissue sections into a retrieval box, and then add an appropriate amount of diluted EDTA retrieval solution (pH 9.0) to immerse the tissue.

4. Microwave at mid-range for 10 minutes retrieval (start timing when the liquid boils), do not let the tissue dry during this process.

5. Take the retrieval box out of the microwave oven and let it cool down naturally; when the retrieval solution has cooled to room temperature, take out slides and rinse them with PBS (pH 7.4) 3 times for 3 minutes each time (do not rinse against the tissues during the rinse process, to avoid breaking the tissues).

6. Add, dropwise, prepared 3% hydrogen peroxide (30% hydrogen peroxide diluted in deionized water) on the sliced tissues to block endogenous peroxidase, incubate at room temperature for 15 min, rinse with PBS three times, 3 minutes each time.

7. Remove PBS with absorbent paper, add 10% goat serum (same or similar to the source of the secondary antibody) dropwise on the slides, and block at 37° C. for 60 min.

8. Dry the liquid around the tissue on the slides with absorbent paper, draw a circle around the tissues with an oily pen, then add the diluted primary antibody dropwise, and incubate at 4° C. overnight in a hydrated box.

9. Rinse the sections with PBS three times for 3 min each time, dry the sections with absorbent paper, add horseradish peroxidase-labeled secondary antibody dropwise, and incubate at room temperature for 60 min.

10. Rinse the sections with PBS three times for 3 min each time, shake off the PBS liquid, dry the sections with absorbent paper, add freshly prepared DAB color developing solution dropwise to each section, observe under a microscope, rinse the sections with tap water to stop color development after a positive signal.

11. Counterstain with hematoxylin for 1 min, rinse with water, differentiate with acidic ethanol differentiation solution, rinse with tap water and return to blue.

12. After rinsing the sections in water, put the sections in sequence in: 70% ethanol-80% ethanol-90% ethanol-95% ethanol-absolute ethanol I-absolute ethanol II-xylene I-xylene II for dehydration and transparentizing, 2 min in each reagent, and finally air-dried the sections in a fume hood.

13. Mount the slides with neutral balsam and cover with coverslips, and place in a fume hood to dry.

14. Observe the dried sections under a microscope or take pictures.

Figure 4A:
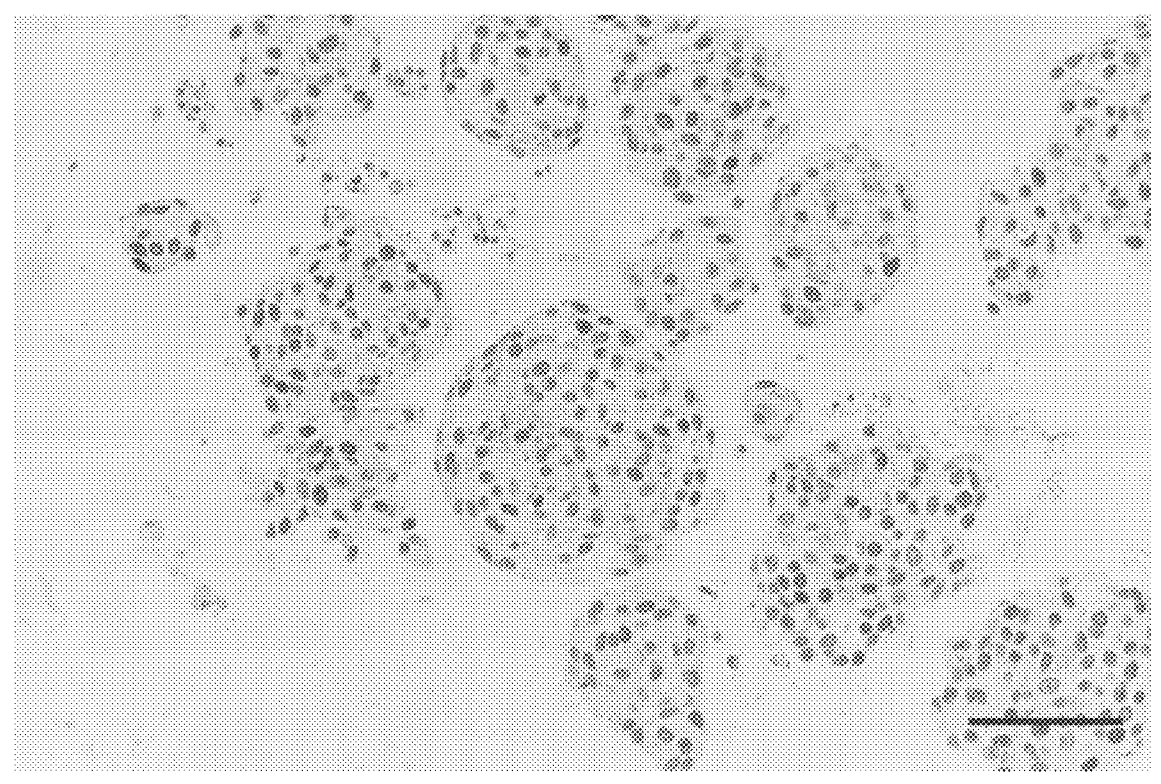
FIGS. 4A and 4B shows the immunohistochemical staining results of the paraffin sections of tumor cell clumps obtained after primary culture of a breast cancer tissue. Scale bar=100 μm for 200×magnification. Panel
Figure 4B:
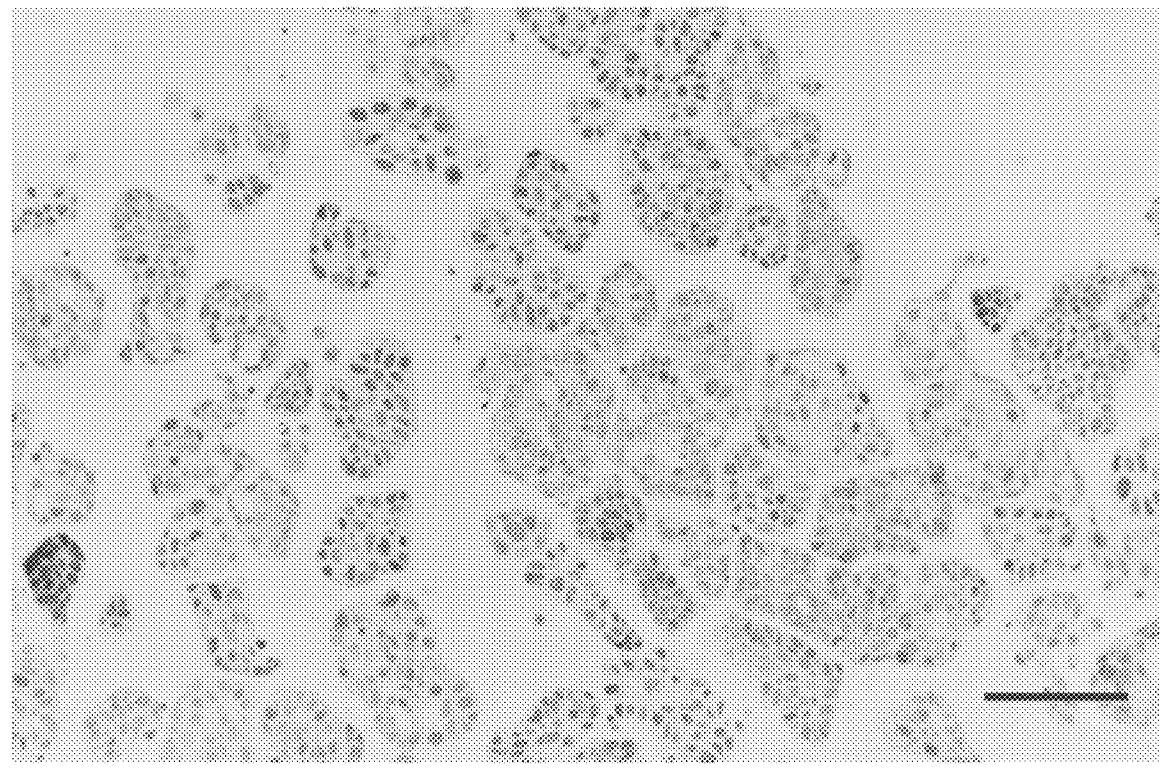

FIG. 4 shows the immunohistochemical staining results of primary breast cancer cell clumps cultured in vitro. It can be seen that the cells that made up the cell clumps were ER positive, which was consistent with the pathological results of the patient, indicating that the cultured tumor cells by this method are of higher purity.

Example 13. In Vitro Culture of Primary Tumor Cells of Different Types of Gynecological Tumor Samples In this example, the operation method and process of primary culture of all samples are completely the same (refer to the above), and only the pathological types of the samples are different. See Table 26 for the samples tested.

TABLE 26

In vitro culture of primary tumor cells of various pathological types of gynecological tumors

| Pathological type | Sample size | Culture success rate |
|---|---|---|
| Breast cancer (surgical samples) | 45 | 39/45 |
| Breast Cancer (puncture samples) | 25 | 19/25 |
| Breast cancer (pleural effusions samples) | 6 | 6/6 |
| Breast cancer (pericardial effusions samples) | 4 | 4/4 |
| Ovarian cancer (surgical samples) | 23 | 18/23 |
| Ovarian cancer (ascites samples) | 9 | 8/9 |
| Endometrial cancer (surgical samples) | 11 | 8/11 |
| Endometrial cancer (biopsy samples) | 3 | 3/3 |
| Cervical cancer (surgical samples) | 5 | 5/5 |
| Cervical cancer (biopsy sample) | 1 | 1/1 |

It can be seen that this method can achieve a very high success rate for in vitro culture of primary tumor cells for various types of gynecological solid tumor samples.

Example 14. Primary Gynecological Tumor Cell Culture Using CYTOP-Modified Cell Culture Consumables In this example, the operation method and process of primary culture of all samples are completely the same (refer to the above), the modification method of CYTOP is completely the same, only the material of cell culture consumables is different (Table 27).

CYTOP modification protocol:

etch the cell culture container with pure oxygen for 3 minutes at a power of 20 W; then cover the surface of the cell culture dish or culture plate with an appropriate amount of 1% CYTOP solution (taking a 96-well plate as an example, 20 μL per well, the appropriate amount means completely covering the bottom of the culture dish), and dry the 1% CYTOP solution, thereby completing the CYTOP modification.

TABLE 27

Effects of CYTOP modified consumables on the culture of primary gynecological tumor cells

| No. | Sample name | PS | PS CYTOP modification |
|---|---|---|---|
| 1 | 20181128HXX5443 | Fail | Success |
| 2 | 20181129XYX6034 | Success | Success |
| 3 | 20181129YWG7181 | Fail | Success |
| 4 | 20181129XSJ8574 | Fail | Fail |
| 5 | 20181130CY8942 | Fail | Success |
| 6 | 20181204LAE5472 | Fail | Success |
| 7 | 20181204WZX6408 | Fail | Success |
| 8 | 20181205CAN9838 | Fail | Success |
| 9 | 20181205WGM6905 | Fail | Success |
| 10 | 20181206HDJ5924 | Fail | Success |
| | Success rate | 1/10 | 9/10 |

Note:
Polystyrene (abbreviated as PS).

It can be seen from Table 27 that CYTOP modification greatly improved the success rate of sample culture.

Example 15. Microwell Plate Chip Processing

In this example, injection molding is used to process PMMA materials (or materials such as PS, PC, COC, COP, LAS, etc.) to obtain a microwell plate chip for culturing primary gynecological tumor cells of the present invention. The chip can be used for primary gynecological tumor cell culture and in vitro drug sensitivity detection experiments. The microplate chip design drawing is shown in FIG. 5.

Figure 5:
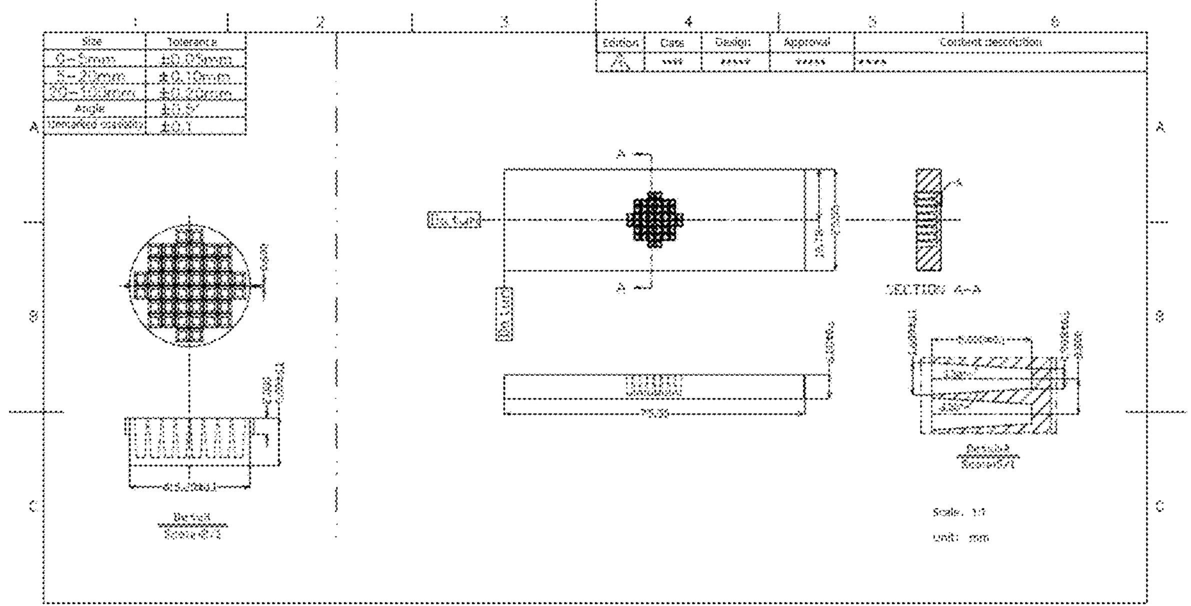
FIG. 5 is a design diagram of the microwell plate chip of the present invention.

In practice, PMMA material (or PS, PC, COC, COP, LAS, etc.) is used to prepare the structure of the microwell plate chip whose design drawing is shown in FIG. 5, and then the above-mentioned CYTOP modification method (see Example 14) is carried out to modify the surface with CYTOP, thereby obtaining the microwell plate chip that can be used for the culture of primary gynecological tumor cells.

INDUSTRIAL APPLICATION

The present invention provides a method for extracting and culturing primary gynecological tumor cells from fresh gynecological tumor surgical samples or puncture biopsy samples or pleural effusions and ascites samples and reagents used therein. The method has the following advantages:

1. The amount of tissue samples is small, only about 20 mg of surgical samples of gynecological solid tumor is needed;
2. The culture period is short, and it only takes 3-10 days to obtain primary tumor cells of the order of $10^7$;
3. The culture stability is high, and the success rate of in vitro culture of qualified gynecological solid tumor surgical samples by this method is as high as 70%;
4. The cell purity is high. In the primary gynecological tumor cell culture obtained by this method, the proportion of tumor cells can reach 70%-95%, and the interference of other cells is less.

The primary gynecological tumor cell culture obtained by the method of the present invention can be used for various cell-based in vitro experiments, second-generation sequencing, construction of animal models, construction of cell lines and the like. It is foreseeable that this culture method has broad application prospects in the fields of gynecological tumor research and clinical diagnosis and treatment.

The invention claimed is:

1. A culture medium for culturing primary gynecological tumor cells, which is culture medium B;

the culture medium B consists of a solution containing three antibiotic/antimycotic agents consisting of penicillin, streptomycin and amphotericin B, 4-(2-hydroxyethyl)-1-piperazineethanesulfonic acid (HEPES), L-alanyl-L-glutamine, human recombinant protein epidermal growth factor (EGF), human recombinant protein basic fibroblast growth factor (bFGF), human recombinant protein hepatocyte growth factor (HGF), human recombinant protein macrophage-stimulating protein (MSP), N-acetyl-L-cysteine, N-2 Supplement, Y-27632, progesterone, β-estradiol and a basic culture medium for human cell culture; wherein:

the final concentration of penicillin in the solution containing three antibiotic and antimycotic agents is 100-200 U/mL;

the final concentration of streptomycin in the solution containing three antibiotic and antimycotic agents is 100-200 μg/mL;

the final concentration of amphotericin B in the solution containing three antibiotic and antimycotic agents is 250-250 ng/ml;

the final concentration of HEPES is 8-12 mM;

the final concentration of L-alanyl-L-glutamine is 0.8-1.2% (v/v);

the final concentration of the human recombinant protein EGF is 10-100 ng/ml;

the final concentration of the human recombinant protein bFGF is 10-50 ng/ml;

the final concentration of the human recombinant protein HGF is 5-25 ng/ml;

the final concentration of the human recombinant protein MSP is 5-25 ng/ml;

the final concentration of N-acetyl-L-cysteine is 0.5-2 mM;

the final concentration of N-2 Supplement is 1% (v/v);

the final concentration of Y-27632 is 5-20 μM;

the final concentration of progesterone is 50-100 nM;

the final concentration of β-estradiol is 10-50 nM; with a balance of the culture medium B comprising the basic culture medium for human cell culture.

2. The culture medium according to claim 1, wherein the components of the culture medium exist separately.

3. The culture medium according to claim 2, wherein in the culture medium B, the human recombinant protein EGF, the human recombinant protein bFGF, the human recombinant protein HGF, the human recombinant protein MSP, N-acetyl-L-cysteine, Y-27632, progesterone, and β-estradiol are provided in mother solutions.

4. The culture medium according to claim 3, wherein the mother solutions are 1,000-100,000-fold mother solutions;

1,000×Human recombinant protein EGF stock solution is composed of human recombinant protein EGF, bovine serum albumin (BSA) and phosphate-buffered saline (PBS), wherein the final concentration of the human recombinant protein EGF is 20 μg/mL, the final concentration of BSA is 0.01 g/mL, and the rest is PBS;

1,000×Human recombinant protein bFGF stock solution is composed of human recombinant protein bFGF, BSA and PBS, wherein the final concentration of the human recombinant protein bFGF is 20 μg/mL, the final concentration of BSA is 0.01 g/mL, and the rest is PBS;

1,000×Human recombinant protein HGF stock solution is composed of human recombinant protein HGF, BSA and PBS, wherein the final concentration of the human recombinant protein HGF is 20 μg/mL, the final concentration of BSA is 0.01 g/mL, and the rest is PBS;

1,000×Human recombinant protein MSP stock solution is composed of human recombinant protein MSP, BSA and PBS, wherein the final concentration of the human recombinant protein MSP is 20 g/mL, the final concentration of BSA is 0.01 g/mL, and the rest is PBS;

1,000×N-acetyl-L-cysteine stock solution is composed of N-acetyl-L-cysteine and water, wherein the concentration of the N-acetyl-L-cysteine is 0.5 M, and the rest is water:

1,000×Y-27632 is composed of Y-27632 and water, wherein the final concentration of Y-27632 is 10 mM, and the rest is water;

100,000×progesterone stock solution is composed of progesterone and absolute ethanol, wherein the final concentration of progesterone is 1 mM, and the rest is absolute ethanol; and 100,000×β-estradiol stock solution is composed of β-estradiol and absolute ethanol, wherein the final concentration of β-estradiol is 1 mM, and the rest is absolute ethanol.

5. The culture medium according to claim 4, wherein in 1,000×Human recombinant protein EGF stock solution, 1,000×Human recombinant protein bFGF stock solution, 1,000×Human recombinant protein HGF stock solution and 1,000×Human recombinant protein MSP stock solution, BSA is provided in a mother solution.

6. The culture medium according to claim 5, wherein BSA is provided in the form of a 100-fold mother solution, 100×BSA solution is composed of BSA and PBS, wherein the final concentration of BSA is 0.1 g/mL, and the rest is PBS.

7. The culture medium according to claim 1, wherein the basic culture medium for human cell culture is Dulbecco's Modified Eagle Medium (DMEM/F12) medium;

or, wherein the culture medium is used for culturing primary gynecological tumor cells.

8. A reagent set for culturing primary gynecological tumor cells, containing the culture medium according to claim 1 and at least one of the following reagents: a sample dissociation solution, a sample preservation solution, a cell isolation buffer, a cell digestion solution, a sample washing solution, a digestion stop solution, a cell cryopreservation medium and 1% CYTOP solution:

the sample dissociation solution is composed of collagenase I, collagenase III, collagenase IV and phosphate-buffered saline (PBS); wherein, the final concentration of collagenase I in the sample dissociation solution is 150-250 U/mL; the final concentration of collagenase III in the sample dissociation solution is 250-350 U/mL; the final concentration of collagenase IV in the sample dissociation solution is 150-250 U/FmL; and the rest is PBS;

the sample preservation solution is composed of fetal bovine serum, two antibiotics penicillin-streptomycin (P/S), 4-(2-hydroxyethyl)-1-piperazineethanesulfonic acid (HEPES) and Hank's Balanced Salt Solution (HBSS); wherein, the final concentration of the fetal bovine serum is 1-5% (v/v); the final concentration of penicillin in the two antibiotics P/S is 100-200 U/mL; the final concentration of streptomycin in the two antibiotics P/S is 100-200 μg/mL; the final concentration of HEPES is 8-12 mM; and the rest is HBSS;

the cell isolation buffer is composed of two antibiotics P/S, heparin sodium and PBS; wherein, the final concentration of penicillin in the two antibiotics P/S is 100-200 U/mL; the final concentration of streptomycin in the two antibiotics P/S is 100-200 μg/mL; the final concentration of heparin sodium is 10 IU/mL; and the rest is PBS;

the composition of the cell digestion solution is as follows: each 10 mL of the cell digestion solution contains 4-6 mL of an enzymatic dissociation reagent, ethylenediaminetetraacetic acid (EDTA) with a final concentration of 5 mM, 1.5-2.5 mL of a recombinant dissociation solution, and the rest is PBS;

the sample washing solution is composed of two antibiotics P/S and PBS; wherein, the final concentration of penicillin in the two antibiotics P/S is 100-200 U/mL; the final concentration of streptomycin in the two antibiotics P/S is 100-200 μg/mL; and the rest is PBS;

the digestion stop solution is composed of fetal bovine serum, two antibiotics P/S and Dulbecco's Modified Eagle Medium (DMEM) medium; wherein, the final concentration of the fetal bovine serum is 8-12%; the final concentration of penicillin in the two antibiotics P/S is 100-200 U/mL; the final concentration of streptomycin in the two antibiotics P/S is 100-200 μg/mL; and the rest is DMEM medium;

the cell cryopreservation medium is composed of Advanced DMEM/F12 medium, dimethyl sulfoxide (DMSO) and 1% methylcellulose solution; wherein, the volume ratio of Advanced DMEM/F12 medium to DMSO to 1% methylcellulose solution is 20:2: (0.8-1.2); 1% methyl cellulose solution is an aqueous methylcellulose solution with a concentration of 1 g/100 ml; and the composition of 1% CYTOP solution is as follows: each 100 mL of 1% CYTOP solution contains 1 mL CYTOP, and the rest is fluorine oil.

9. A method for culturing primary gynecological tumor cells, comprising the step of:

(1) obtaining primary gynecological solid tumor cells or primary tumor cells in gynecological tumor pleural effusions and ascites samples;

wherein the primary gynecological solid tumor cells are obtained by dissociating gynecological solid tumor tissue with the sample dissociation solution;

the primary tumor cells in gynecological tumor pleural effusions and ascites samples are isolated from the gynecological tumor pleural effusions and ascites samples with the cell isolation buffer;

wherein the sample dissociation solution comprises:

a collagenase I having a final concentration of 150-250 U/mL, a collagenase III having a final concentration of 250-350 U/mL, a collagenase IV having a final concentration of 150-250 U/mL, and a phosphate-buffered saline (PBS) as a remainder of the sample dissociation solution;

the cell isolation buffer comprises:

two antibiotics penicillin-streptomycin (P/S);

wherein, the final concentration of penicillin in the two antibiotics P/S is 100-200 U/mL; the final concentration of streptomycin in the two antibiotics P/S is 100-200 μg/mL;

heparin sodium having a final concentration of 10 IU/mL, and

PBS as a remainder of the cell isolation buffer;

(2) conducting a suspension culture with a culture medium on the primary gynecological solid tumor cells or primary tumor cells in gynecological tumor pleural effusions and ascites samples obtained in step (1);

wherein the culture medium consists of:

a solution containing three antibiotic and antimycotic agents, 4-(2-hydroxyethyl)-1-piperazineethanesulfonic acid (HEPES), L-alanyl-L-glutamine, human recombinant protein epidermal growth factor (EGF), human recombinant protein basic fibroblast growth factor (bFGF), human recombinant protein hepatocyte growth factor (HGF), human recombinant protein macrophage-stimulating protein (MSP), N-acetyl-L-cysteine, N-2 Supplement,

Y-27632, progesterone,

β-estradiol, and a basic culture medium for human cell culture;

wherein, a final concentration of penicillin in the solution containing three antibiotic and antimycotic agents is 100-200 U/mL;

a final concentration of streptomycin in the solution containing three antibiotic and antimycotic agents is 100-200 μg/mL;

a final concentration of amphotericin B in the solution containing three antibiotic and antimycotic agents is 250-250 ng/ml;

a final concentration of HEPES is 8-12 mM;

a final concentration of L-alanyl-L-glutamine is 0.8-12% (v/v);

a final concentration of the human recombinant protein EGF is 10-100 ng/ml;

a final concentration of the human recombinant protein bFGF is 10-50 ng/ml;

a final concentration of the human recombinant protein HGF is 5-25 ng/ml;

a final concentration of the human recombinant protein MSP is 5-25 ng/ml;

a final concentration of N-acetyl-L-cysteine is 0.5-2 mM;

a final concentration of N-2 Supplement is 1% (v/v);

a final concentration of Y-27632 is 5-20 μM;

a final concentration of progesterone is 50-100 nM; and a final concentration of β-estradiol is 10-50 nM.

10. The method according to claim 9, wherein, in the method, the sample dissociation solution is used to dissociate gynecological solid tumor tissue according to a method comprising the following steps:

according to the dosage of 0.1-0.3 ml, of the sample dissociation solution per mg of tissue, treating the gynecological solid tumor tissue that has been chopped with the sample dissociation solution pre-heated at 37° C. to conduct sample dissociation at 37° C. for 15 minutes to 3 hours;

or, wherein, in the method, the isolation buffer is used to isolate the gynecological tumor pleural effusions and ascites samples according to a method comprising the following steps:

suspending the cells in the gynecological tumor pleural effusions and ascites samples in the cell isolation buffer, and then obtaining the primary tumor cells in gynecological tumor pleural effusions and ascites samples by density gradient centrifugation.

11. The method according to claim 9, wherein in the method, the primary gynecological tumor cell culture medium is used to conduct the suspension culture of the primary gynecological tumor cells according to a method comprising the following steps:

in a cell culture container M, suspending the primary gynecological tumor cells using the primary gynecological tumor cell culture medium and culturing the cells at 37° C. and 5% $CO_2$, and changing the culture medium every 2-4 days;

wherein the cell culture container M is any one of the following Groups (I) or (II):

Group (I) comprising a cell culture container made of polystyrene, a cell culture container made of polycarbonate, a cell culture container made of polymethyl methacrylate, a cell culture container made of cyclic olefin copolymer (COC) resin, a cell culture container made of cycloolefin polymer, or a cell culture container with a low-attachment-surface, or Group (II) comprising a cell culture container obtained by modifying a cell culture container from Group (I) by cyclized transparent optical polymer (CYTOP), or wherein the cell culture container is a cell culture dish, a cell culture plate, or a microwell plate chip configured for culturing cells.

12. The method according to claim 11, wherein, in Group (II), the CYTOP modification is performed on the cell culture container selected from Group (I) according to a method comprising the following steps:

etching the cell culture container selected from Group (I) with pure oxygen for 3 minutes at a power of 20 W to obtain an etched cell culture container;

then covering the surface of the etched cell culture container with the 1% CYTOP solution; and drying the 1% CYTOP solution to obtain a CYTOP modified cell culture container.

13. The method according to claim 9, wherein the method further comprises a step of treating the gynecological solid tumor tissue prior to dissociation by:

washing the surface of the gynecological solid tumor tissue sample with 70-75% (v/v) ethanol;

washing the gynecological solid tumor tissue sample with the sample washing solution; and then washing the gynecological solid tumor tissue sample with sterile PBS solution;

and/or, wherein the gynecological solid tumor tissue sample subjected to the treatment prior to dissociation is within 2 hours after excision and the gynecological solid tumor tissue sample has been kept in the sample preservation solution before the treatment prior to dissociation is performed; and/or, wherein in the method, after dissociating the gynecological solid tumor tissue with the sample dissociation solution, the following steps are further comprised:

terminating the dissociation reaction using the digestion stop solution, and collecting the cell suspension;

filtering the cell suspension to remove tissue debris and adherent cells;

centrifuging the cell suspension and then resuspending the cells in sterile PBS; and centrifuging and then resuspending the cell pellet in the culture medium.

14. The method according to claim 9, wherein in the process of culturing the primary gynecological tumor cells with the culture medium, the method further comprises the following step:

when the primary gynecological tumor cells form clumps with a diameter of 80-120 μm, passaging the primary gynecological tumor cells.

15. The method according to claim 14, wherein the method further comprises the steps of cryopreserving and/or resuscitating the primary gynecological tumor cells after 2-3 passages and expansions.

16. The culture medium according to claim 1, wherein the gynecological tumor is breast cancer, ovarian cancer, endometrial cancer, cervical cancer or metastatic lesions thereof.

* * * * *